(12) United States Patent
Yeung

(10) Patent No.: US 10,036,752 B2
(45) Date of Patent: Jul. 31, 2018

(54) AGENTS AND METHODS FOR DETERMINING COLORECTAL CANCER STATUS

(71) Applicant: OXFORD UNIVERSITY INNOVATION LIMITED, Botley Oxford (GB)

(72) Inventor: Trevor Ming-Yee Yeung, Headington Oxford (GB)

(73) Assignee: Oxford University Innovation Limited, Botley, Oxford (GB)

( * ) Notice: Subject to any disclaimer, the term of this patent is extended or adjusted under 35 U.S.C. 154(b) by 0 days.

(21) Appl. No.: 15/321,572

(22) PCT Filed: Jun. 26, 2015

(86) PCT No.: PCT/GB2015/051867
§ 371 (c)(1),
(2) Date: Dec. 22, 2016

(87) PCT Pub. No.: WO2015/198065
PCT Pub. Date: Dec. 30, 2015

(65) Prior Publication Data
US 2017/0146537 A1 May 25, 2017

(30) Foreign Application Priority Data
Jun. 26, 2014 (GB) .................................. 1411393.0

(51) Int. Cl.
| | |
|---|---|
| A61K 38/00 | (2006.01) |
| C12N 5/00 | (2006.01) |
| G01N 33/574 | (2006.01) |
| A61K 49/00 | (2006.01) |
| A61B 5/00 | (2006.01) |
| A61N 5/10 | (2006.01) |
| A61K 47/64 | (2017.01) |

(52) U.S. Cl.
CPC ..... *G01N 33/57419* (2013.01); *A61B 5/0071* (2013.01); *A61B 5/4255* (2013.01); *A61B 5/4839* (2013.01); *A61K 47/6415* (2017.08); *A61K 49/0032* (2013.01); *A61K 49/0043* (2013.01); *A61K 49/0056* (2013.01); *A61N 5/10* (2013.01); *G01N 2333/4724* (2013.01); *G01N 2333/4725* (2013.01); *G01N 2440/38* (2013.01)

(58) Field of Classification Search
CPC .................................................... A61K 38/00
USPC ......................................... 514/19.3; 435/325
See application file for complete search history.

(56) References Cited

U.S. PATENT DOCUMENTS

| | | | | |
|---|---|---|---|---|
| 6,110,891 A | * | 8/2000 | Pusztai ................... | A61K 38/18 424/85.1 |
| 2006/0251580 A1 | * | 11/2006 | Keppler ............... | A61K 49/085 424/1.49 |
| 2012/0282628 A1 | * | 11/2012 | Ahn ................. | G01N 33/57484 435/7.8 |
| 2015/0329602 A1 | * | 11/2015 | Sato ....................... | C07K 14/42 435/69.1 |

FOREIGN PATENT DOCUMENTS

WO 2009/075864 A1 6/2009

OTHER PUBLICATIONS

Aksoy et al., "Characterisation of MUC2 and MUC5AC mucins from a colorectal adenoma-mucinous carcinoma sequence: in vitro evidence for the neotransformation", Biyokimya Dergisi 24(2) 3-9 (1999).
Bernstein et al., "Patchy field defects of apoptosis resistance and dedifferentiation in flat mucosa of colon resections from colon cancer patients", Ann Surg Oncol 9(5) 505-507 (2002).
Boland et al., "A cancer-associated mucin alteration in benign colonic polyps", Gastroenterology 82(4) 664-672 (1982).
Brink et al., "Detection of inflammation- and neoplasia-associated alterations in human large intestine using plant/invertebrate lectins, galectin-1 and neoglycoproteins", Acta Anat 161(1-4) 219-233 (1998).
Coic et al., "Design of a specific colonic mucus marker using a human commensal bacterium cell surface domain", J Biol Chem 287(19) 15916-15922 (2012).
Fu et al., "Loss of intestinal core 1-derived O-glycans causes spontaneous colitis in mice", J Clin Invest 121(4) 1657-1666 (2011).
Grootjans et al., "Ischaemia-induced mucus barrier loss and bacterial penetration are rapidly counteracted by increased goblet cell secretory activity in human and rat colon", Gut 62(2) 250-258 (2013).
Herrmann, "Intestinal mucins: Soluble and insoluble problems", XP002744496, retrieved from STN accession No. AAIC805303, Database accession No. 2002:298 abstract Dissertation Abstracts International vol. 62(2C) 2000 p. 253 (Abstract Only).
Kocer et al., "Clinical Value of MUC 2 Expression in Colorectal Carcinoma", Nagoya Med. J. 45:75-87 (2001).
Latella et al., "Characterization of the mucins produced by normal human colonocytes in primary culture", Int J Colorectal Dis 11(2) 76-83 (1996).
Liquori et al., "In situ characterization of O-linked glycans of Muc2 in mouse colon", Acta Histochem 114(7) 723-732 (2012).
Orntoft et al., "A two-site lectinoenzymatic assay for determination of tumour marker glycoproteins in rectal secretions", Glycocon. J. 14(2) 191-199 (1997).
Rhodes et al., "Glycoprotein abnormalities in colonic carcinomata, adenomata, and hyperplastic polyps shown by lectin peroxidase histochemistry", J Clin Pathol 39(12) 1331-1334 (1986).
Wei et al., "Fatty acid synthase modulates intestinal barrier function through palmitoylation of mucin 2", Cell Host Microbe 11(2) 140-152 (2012).

* cited by examiner

*Primary Examiner* — Raymond J Henley, III
(74) *Attorney, Agent, or Firm* — Mark J. FitzGerald; Nixon Peabody LLP

(57) ABSTRACT

The invention provides a method of determining the colorectal cancer status of subject, comprising applying to a colon and/or rectal surface an agent which is able to distinguish between a) mature glycosylated forms of MUC2 and b) incomplete or aberrant glycosylated forms of MUC2, and determining the extent to which the agent binds.

13 Claims, 30 Drawing Sheets

Figure 9
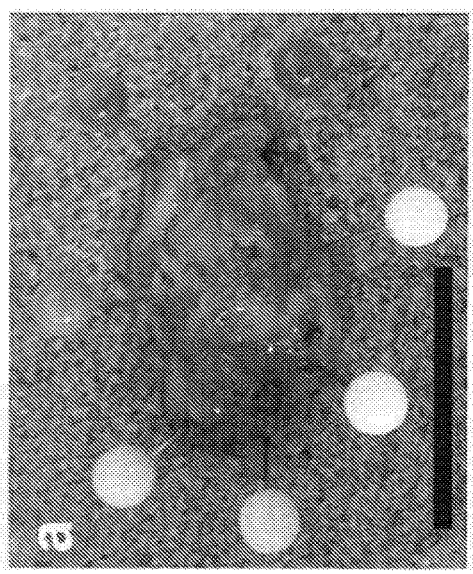
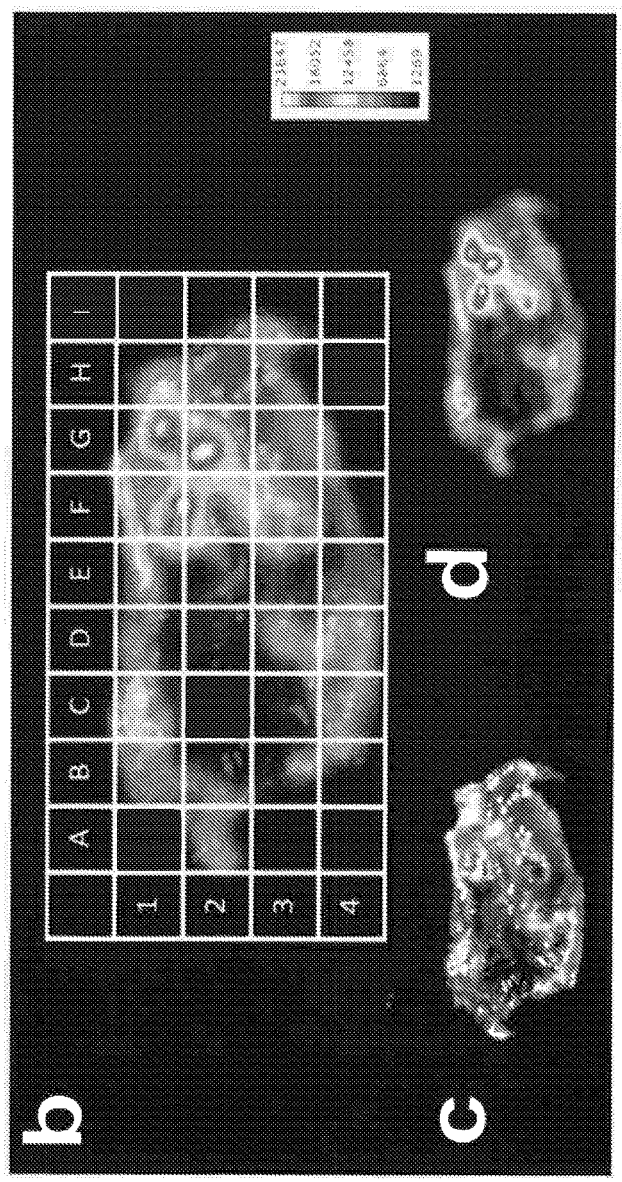

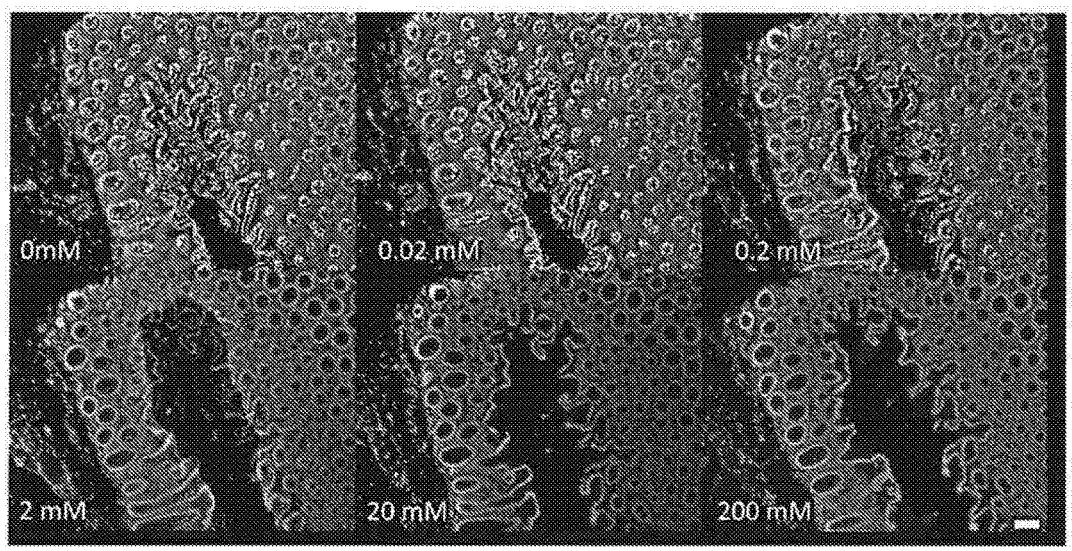
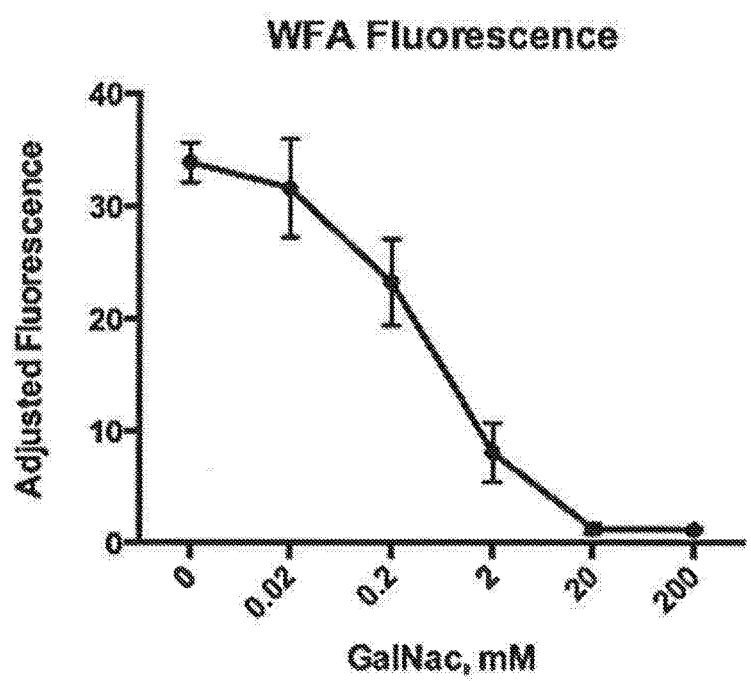
Figure 13

IVIS Camera
Sigmoid
Diverticular Disease

Quantitation of Whole Organ Fluorescent Imaging

| Sample | 1 | 2 | 3 | 4 | 5 |
|---|---|---|---|---|---|
| Indication | Caecal AdenoCA | Rectosigmoid AdenoCA | Chronic UC with Transverse Colon AdenoCA | Chronic UC with DALM, distal sparing disease | Diverticular disease |
| Treatment | Right hemicolectomy | Anterior resection | Left hemicolectomy | Total colectomy | Rectosigmoid resection |
| Pathology | Moderately differentiated pT3N0Mx Dukes B | Moderately differentiated pT4N2Mx Dukes C1 | Moderately differentiated pT4N0Mx Dukes B | Active chronic UC, moderate activity with DALM | Moderately differentiated activity with Diverticulosis |
| Normal:Cancer Fluorescence Ratio^ | 3.2 ± 0.2 | 2.2 ± 0.2 | 3.1 ± 0.1 | 1.7 ± 0.1 | N/A |
| Background Fluorescence | 1340.7 ± 34.7 | 1185.4 ± 7.3 | 1250.4 ± 31.6 | 1059.5 ± 2.9 | 1064.5 ± 4.5 |
| Normal colonic mucosa ^^ | 4063.8 ± 157.4 | 3475.2 ± 151.7 | 4527.6 ± 144.7 | 1965.3 ± 83.6 | 3343.4 ± 282.2 |
| Dysplasia | | | 1706.9 ± 36.3 | 1134.2 ± 7.6 | |
| Carcinoma | 1255.7 ± 37.9 | 1577.6 ± 87.4 | 1486.2 ± 27.5 | | |
| Inflammation | | | | 1596.0 ± 60.0 | |
| Diverticular | | | | | 3207.5 ± 124.3 |
| DALM | | | | 1174.0 ± 12.6 | |

^Normal:cancer fluorescence ratio (samples 1,2,3) or normal:dysplasia ratio (sample 4). No CA/dysplasia in sample 5 to do this calculation. Mean ratio=2.6
^^ normal colonic mucosa for sample 4 is distal spared colonic mucosa on background of UC

Figure 25

Quantitation using fluorescence endoscope system

| Sample | 1 | 2 | 3 | 4 | 5* | 6* |
|---|---|---|---|---|---|---|
| Indication | Rectosigmoid cancer | Recurrent rectal cancer, previous polypectomy and RT | Multiple left sided polyps | Ulcerative colitis, DALM | Rectosigmoid Cancer | Caecal cancer |
| Treatment | Anterior resection | Transanal endoscopic microsurgery | Anterior resection | Anterior resection | Anterior resection | Right hemicolectomy |
| Pathology | Moderately differentiated pT4N0Mx Dukes B | Moderately differentiated pT1NxMx | Tubular adenomas Low grade dysplasia | DALM with synchronous well differentiated adenocarcinoma pT2N0M0 Dukes A pT1N0M0 Dukes A | Moderately differentiated pT4N0Mx Dukes B | Poorly differentiated pT4bN1M0 Dukes C2 |
| Normal to Cancer Fluorescence Ratio^ | 4.0 ± 0.4 | 6.0 ± 0.5 | 2.8 ± 0.4 | 2.7 ± 0.1 | 2.6 ± 0.4 | 3.7 ± 0.5 |
| Background Fluorescence | 2.2 ± 1.8 | 1.3 ± 0.5 | 1.1 ± 0.8 | 12.6 ± 0.5 | 27.0 ± 0.9 | 22.9 ± 0.7 |
| Normal colonic mucosa | 116.3 ± 4.3 | 102.2 ± 9.3 | 130.7 ± 3.9 | 152.4 ± 0.7 | 198.3 ± 0.6 | 207.0 ± 3.3 |
| Dysplasia | | 47.1 ± 4.7 | 47.3 ± 6.6 | 69.2 ± 7.8 (DALM) | | |
| Carcinoma | 28.9 ± 1.5 | 17.0 ± 1.1 | | 57.3 ± 1.2 | 77.9 ± 11.3 | 57.2 ± 7.0 |

RT = radiotherapy
^Normal:cancer fluorescence ratio(samples 1, 2, 4, 5 and 6) or normal:dysplasia fluorescence ratio (sample 3). Mean ratio = 3.6
*Specimens visualized under simulated colonoscopic conditions

Figure 30

AGENTS AND METHODS FOR DETERMINING COLORECTAL CANCER STATUS

CROSS-REFERENCE TO RELATED APPLICATIONS

This application is a 35 U.S.C. § 371 National Phase Entry Application of International Application No. PCT/GB2015/051867, filed Jun. 26, 2015, which designates the U.S. and which claims priority to GB Application No. 1411393.0, filed Jun. 26, 2014, the contents of each of which are incorporated herein by reference in their entireties.

The present invention relates to agents and methods for determining the colorectal cancer status of a subject.

In the UK over 40,000 patients are diagnosed with colorectal cancer each year. Colonoscopy is an important diagnostic and therapeutic procedure in the management of colorectal cancer. The gold standard has been white-light endoscopy for screening the general population and for surveillance of patients at high risk of developing cancer. Early detection of colorectal lesions in screening colonoscopy and sigmoidoscopy has been shown to reduce colorectal cancer mortality. However, the detection of flat and depressed neoplasms presents a particular challenge. Recent developments to aid the detection and characterization of dysplastic lesions include chromoendoscopy, narrow band imaging (NBI), auto-fluorescence (AFI) and confocal endomicroscopy.

The development of an adjunct tool to specifically identify premalignant colorectal dysplasia and cancer, and to help distinguish benign hyperplastic polyps (HPs) from significant lesions such as sessile serrated polyps (SSPs) and traditional serrated adenomas (TSAs), has the potential to reduce the incidence of false negatives and would be highly desirable.

In addition, a key issue during transanal endoscopic microsurgery (TEMS) and endoscopic mucosal resection (EMR) is to determine where the resection margin should be, that is where the tumor or dysplasia tissue ends and normal tissue begins. Using conventional white light visualisation it is often difficult to discern where that margin should be, particularly for flat or carpet-like lesions. A tool that could distinguish dysplastic or cancerous tissue from normal tissue would therefore allow complete resection of abnormal tissue and would be highly desirable.

It is an aim of the present invention therefore to provide an adjunct tool to allow the colorectal cancer status of a subject or sample to be determined, and also to provide a means to more accurately define resection margins in a subject or sample with abnormal, tumorigenic or dysplastic tissue. The invention may be used to determine whether a subject has colorectal cancer or colorectal dysplasia, and/or to determine the appropriate treatment and/or prognosis for a particular subject. The invention may also be used to monitor cancer or dysplasia progression or the effectiveness of a treatment for colorectal cancer or dysplasia.

According to a first aspect, the present invention provides a method of determining the colorectal cancer status of subject, comprising applying to a colon or rectal surface an agent which is able to distinguish between a) mature glycosylated forms of MUC2 and b) incomplete or aberrant glycosylated forms of MUC2, and determining the extent to which the agent binds.

In a further aspect the invention provides an agent which is able to distinguish between a) mature glycosylated forms of MUC2 and b) incomplete or aberrant glycosylated forms of MUC2, for use in determining the colorectal cancer status of subject. In particular the agent may be for use in the treatment, diagnosis, prognosis, or monitoring of the progression, of colorectal cancer or dysplasia.

In another aspect the invention provides the use of an agent which is able to distinguish between a) mature glycosylated forms of MUC2 and b) incomplete or aberrant glycosylated forms of MUC2, in the preparation of medicament for determining the colorectal cancer status of a subject. The use may be for the treatment, diagnosis, prognosis, or monitoring of the progression, of colorectal cancer or dysplasia.

Preferably the agent binds only, or predominantly, to mature glycosylated forms of MUC2 or only, or predominantly, to incomplete or aberrant glycosylated forms of MUC2.

Preferably when determining the extent to which the agent binds to the surface of the colon or rectum regions are identified which the agent does or does not bind to, or binds to more preferentially.

The phrase "colorectal cancer status" includes any manifestation of colorectal cancer including colorectal dysplasia. For example, colorectal cancer status includes the presence or absence of colorectal cancer or colorectal dysplasia; the progression of colorectal cancer or colorectal dysplasia; the effectiveness or response of a subject to a treatment for colorectal cancer or colorectal dysplasia; and/or the prognosis for a subject with colorectal cancer or colorectal dysplasia.

The method of the invention may be used, for example, for any one or more of the following: to diagnose colorectal cancer or colorectal dysplasia; to advise on the prognosis of a subject with colorectal cancer or colorectal dysplasia; to diagnoses SSPs and/or TSAs; to diagnose HPs; to distinguish between SSPs/TSAs and HPs; to monitor disease progression; to monitor effectiveness or response of a subject to a particular treatment; and/or to aid in the treatment of colorectal cancer or colorectal dysplasia.

The agent may be applied to a resected or biopsy sample of colorectal tissue ex vivo. Alternatively, the agent may be applied to the colon and/or rectal surface of a subject in vivo, for example, the agent may be topically applied onto the surface of a subject's colon and/or rectum. The agent may be sprayed onto the surface of the colon and/or rectum of a subject. The agent may be applied using an endoscope or a colonoscope, or it may be administered by way of an enema. Alternatively the agent may be administered orally in a capsule or sachet form, and released as part of the bowel preparation prior to colonoscopy or bowel surgery.

The agent may be a protein, a peptide, a small molecule or an antibody. The agent preferably has the ability to distinguish between mucus and other complex glycoproteins found on the epithelial surface of the colon and/or rectal surface that displays mature glycosylation of MUC2 and mucus and other complex glycoproteins found on the epithelial surface where the glycosylation of MUC2 is incomplete or aberrant.

The agent may be a lectin. Lectins are specific carbohydrate recognition proteins. The lectin may be *Wisteria floribunda* agglutinin (WFA) or *Dolichos biflorus* agglutinin (DBA). The lectin, for example WFA or DBA, may preferentially bind to mature glycosylated MUC2 allowing normal tissue to be clearly distinguished from tissue with cancer or dysplasia.

MUC2, also known as Mucin 2, is a protein that in humans is encoded by the MUC2 gene and is part of the mucin protein family. MUC2 is the main mucin protein and it is secreted onto mucosal surfaces from goblet cells in the epithelial lining which secrete MUC2 into the lumen of the large intestine. MUC2, along with small amounts of related-mucin proteins, polymerizes in the colon/large intestine into a gel of which 80% by weight is oligosaccharide side-chains that are added as post-translational modifications to the mucin proteins. This gel provides an insoluble mucous barrier that serves to protect the intestinal epithelium.

Glycosylation of MUC2 changes as a tissue moves from normal to dysplastic to cancerous. More specifically the level of glycosylation reduces or becomes aberrant as a tissue becomes dysplastic or cancerous. This change in glycosylation may mean that agents that bind well to mature glycosylated MUC2 associated with normal tissue, no longer bind, or bind less well, to tissues which have dysplasia, are abnormal (for example have SSPs/TSAs) or are cancerous.

The agent may be labeled to allow it to be more easily visualized. For example the agent may be labeled with a fluorophore. The fluorophore may be fluorescein, rhodamine (TRITC), coumarin, cyanine (eg Cy5 or Cy5.5) or Licor IRDye 800CW Infrared Dye. Alternatively the label could be a radiolabel. The agent may be labeled WFA or labeled DBA.

By using a labeled agent it may be possible to visualise and distinguish areas of a colon/rectum tissue, either in a sample ex vivo or in vivo in a subject, where MUC2 glycosylation is incomplete or aberrant, and regions where glycosylation is complete and mature. Areas of incomplete or aberrant glycosylation of MUC2 may be areas of premalignant dysplasia or cancer or may be SSPs or TSAs. Areas of complete or mature glycosylation of MUC2 may represent regions of normal tissue. By being able to identify these different regions, with different MUC2 glycosylation patterns, a more accurate diagnosis and/or prognosis may be made. Being able to distinguish normal tissue from dysplasia or cancer tissue may also allow a more targeted therapy to be administered. For example, if the area of the cancer or the dysplasia can be clearly seen then administration of therapeutic agents can be more targeted and any surgical intervention can be more accurate. This may have the advantage of reducing the need for repeated treatment or surgical intervention if all the dysplastic or cancerous tissue can be removed or treated in the first instance. It will also reduce the risk of recurrence of the dysplasia or cancer.

The agent may be conjugated to a drug allowing the drug to be delivered to abnormal tissue, assuming the agent preferentially binds to abnormal, dysplastic or cancerous tissue. Alternatively, if the agent targets normal tissues, it may be conjugated to a protective agent to "shield" normal cells from radiation during radiotherapy.

The method of the present invention may be used to identify premalignant colorectal dysplasia and/or cancer. In particular, the method of the present invention may be used to distinguish benign hyperplastic polyps (HPs) from significant lesions such as sessile serrated polyps (SSPs) and traditional serrated adenomas (TSAs). Benign HPs are typically associated with mature glycosylated MUC2, whilst SSPs and TSA are associated with MUC2 with incomplete or aberrant glycosylation. Thus the method of the invention has the potential to reduce the incidence of false negatives in the diagnosis of colorectal cancers, this is particularly important as missed SSPs can result in the development of colorectal cancer via the serrated pathway. Using conventional white light visualization of colorectal tissue it is often very difficult to discern what is a benign HP and what is an SSP or TSA, if they can be seen at all. The method of the invention solves this problem.

The method of the invention may also allow the margins of cancer or dysplasia to be more accurately defined in a sample. Thus allowing more complete and accurate removal of such tissue.

The method of the invention preferably allows normal colorectal mucosa to be distinguished from dysplasia and/or cancer tissue. This may be achieved by taking advantage of the difference in the pattern of glycosylation of MUC2 in abnormal, cancer and dysplastic tissue compared to in normal tissue.

In one embodiment, labelled WFA or DBA can be used to distinguish premalignant colorectal dysplasia and/or cancer from normal tissue. Labelled WFA and DBA will both preferentially bind to mature glycosylated MUC2, thus any labelled tissue may be considered normal and any non-labeled tissue, or significantly reduced labeled tissue, can be considered dysplastic or cancerous, and a fairly distinct demarcation may be visible between the two.

The agent may be formulated for administration by dissolving or dispersing it in a suitable flowable carrier vehicle, such as water, alcohol or an aqueous-alcoholic fluid. The carrier vehicle may be thickened with natural or synthetic thickeners such as gums, acrylates or modified celluloses. The formulation may also comprise an effective amount of a lubricant such as a natural or synthetic fat or oil, i. e., a trisfatty acid glycerate or lecithin. Nontoxic nonionic surfactants can also be included as wetting agents and dispersants.

The agent may be intended to be administered at a dose of less than about 100 µg/mL, preferably less than about 50 µg/mL, more preferably less than about 25 µg/mL, or less than about 20 µg/mL, or less than about 10 µg/mL or about 5 µg/mL.

In a further aspect the invention provides a method of determining the colorectal cancer status of the colorectal region of a subject, comprising topically applying to the region a lectin, such as WFA or DBA, and determining the extent to which it binds. Preferably the lectin is able to distinguish between MUC2 with mature glycosylation and MUC2 with incomplete or aberrant glycosylation.

The lectin may be isolated from a natural source, or it may be recombinantly or chemically synthesized.

If the lectin is WFA or DBA, it is intended that reference to WFA or DBA includes the full length lectin and any functionally derivative thereof, for example a truncated version or a modified version, which retains the ability to distinguish between MUC2 with mature glycosylation and MUC2 with incomplete or aberrant glycosylation.

In another aspect the invention provides a method of treating colorectal cancer or dysplasia in a subject comprising:
  topically applying to the colon and/or rectal region of a subject a labeled agent capable of binding predominantly to either mature glycosylated forms of MUC2 associated with healthy tissue or to incomplete or aberrant glycosylated forms of MUC2 associated with dysplasia or cancer;
  visualizing the colorectal region to which the agent was applied and observing where the agent has bound; and
  excising or treating tissue associated with the incomplete or aberrant glycosylated forms of MUC2.

In an embodiment the agent binds only, or predominantly, to mature glycosylated forms of MUC2 associated with healthy tissue. If in this embodiment the agent is labeled with a fluorophore it will, when illuminated, fluoresce predominantly on the healthy tissue, and any cancerous or dysplastic or abnormal tissue will have little or no fluorescence. By looking at the pattern of fluorescence the demarcation between healthy and dysplastic or cancerous tissue will be much clearer than simply under white light and will allow the more accurate removal of as much of the dysplastic and/or cancerous tissue as possible.

In a further aspect the invention provides a kit for identifying cancerous or dysplastic colorectal tissue in a subject comprising i) a labeled agent which binds predominantly to either mature glycosylated forms of MUC2 or to incomplete or aberrant glycosylated forms of MUC2; and ii) instructions to apply the labeled agent topically to the surface of the colon and/or rectal region of a subject. The agent may be WFA or DBA.

The agent may be intended to be administered via an endoscope. The agent may be as herein described.

In another aspect the invention provides a method of monitoring progression of colorectal cancer or dysplasia in a subject comprising:
i) topically applying to the colon and/or rectal region of a subject a labeled agent capable of binding predominantly to mature glycosylated forms of MUC2 associated with healthy tissue or to incomplete or aberrant glycosylated forms of MUC2 associated with dysplasia or cancer; and
ii) visualizing the colorectal region and observing where the agent has bound; and
iii) at a later time point, repeating steps i) and ii) and determining whether the extent of dysplastic or cancer tissue has changed.

The time between steps ii) and iii) may be a matter of weeks, months or years, preferably at least 1 month, 2 months, 3 months or more.

In an embodiment step iii) is carried out preferably after the administration of a treatment or the removal of some tissue.

Based on the observations in step iii) decisions may be made on the next course of action, for example if the region of dysplasia or cancer has not reduced then further tissue excision may be advised or further chemo or radiotherapy may be advised.

The method of monitoring progression of colorectal cancer or dysplasia in a subject may not comprise any treatment of the subject.

In a further aspect the invention provides an assay for selecting a treatment regimen, the assay comprising:
i) topically applying to the colon and/or rectal region of a subject a labeled agent capable of binding predominantly to mature glycosylated forms of MUC2 associated with healthy tissue or to incomplete or aberrant glycosylated forms of MUC2 associated with dysplasia or cancer;
ii) visualizing the colorectal region and observing where the agent has bound;
iii) determining, based on the binding of the agent, whether a subject has any dysplastic or cancer tissue;
iv) if dysplastic or cancer tissue is present deciding to administer chemotherapy, radiotherapy and/or removal of the dysplastic or cancer tissue.

According to a still further aspect the invention provides an apparatus comprising:
i) an endoscope or colonoscope configured to visualize a particular fluorophore;
ii) the endoscope or colonoscope further comprising a working channel containing an agent as described herein; and
iii) an output module connected to the endoscope or colonoscope for displaying and/or analyzing the images obtained by the endoscope or colonoscope.

The invention further provides the use of an apparatus according to the invention in determining the colorectal cancer status of a subject. The use may comprise inserting the endoscope or colonoscope into the colon or a subject: administering a fluorophore labelled agent capable of distinguishing between a) mature glycosylated forms of MUC2 and b) incomplete or aberrant glycosylated forms of MUC2; observing the pattern of labeled agent binding in the colon; and analyzing the results on the output module. The output module may be a monitor.

In any aspect of the invention the subject may be a human or non-human animal. Preferably the subject is a human. Alternatively, the subject may also be a horse, cow, sheep, primate (eg monkey), goat, dog, cat, rabbit, guinea pig, rat or mouse or any other suitable animal.

The skilled man will appreciate that preferred features of any one embodiment and/or aspect of the invention may be applied to all other embodiments and/or aspects of the invention.

BRIEF DESCRIPTION OF THE DRAWINGS

There now follows by way of example only a detailed description of the present invention with reference to the accompanying drawings, in which:

FIG. 1(a) shows the hierarchical clustering of a mRNA microarray of genes involved in the glycosphingolipid biosynthesis pathway differentially expressed between 30 colorectal cancer cell lines and 22 normal mucosal samples. (Red represents higher expression, blue lower expression). Two genes showed clearly statistically significant higher expression in the normal tissue compared to cancer, B3GALT4 (bonferroni multiple test corrected $p=3.1 \times 10-13$) and ST6GALNAC6 ($p=5.2 \times 10-13$). FIG. 1(b) shows the results of an initial screen of GalNAc binding lectins, based on overall level of fluorescence on tissue microarrays in normal (n=6) and cancer (n=6) samples. Lectins screened included *Amaranthus Caudatus* (ACL), *Bauhinia Purpurea* (BPL), *Wisteria floribunda* (WFA), *Dolichos biflorus* (DBA), *Vicia Villosa* (VVL) and *Sophora Japonica* Agglutinin (SJA). unpaired t-test **$p<0.0001$, *$p<0.001$, *$p<0.05$. FIG. 1(c) illustrates representative examples of images obtained from FFPE sections of normal, low-grade dysplasia (LGD), high grade dysplasia (HGD) and invasive colorectal cancer. Blue (DAPI), Green (WFA-Fluorescein), Red (DBA-Rhodamine) Rhodamine) and merged channels. ×5 objective. Scale bar 200 µm. FIG. 1(d) shows dot plots of fluorescence of WFA-Fluorescein and DBA-Rhodamine for FFPE sections of normal (n=21), LGD (n=21), HGD (n=9) and cancer (n=10) in non-paired specimens. Data in graphs are means+/− SEM. (t-test, **$p<0.0001$). FIG. 1(e) shows examples of images obtained from the FFPE tissue microarray, paired normal (N) and colorectal cancer (C) specimens. DAPI (blue) WFA-fluorescein (green) ×5 objective. Scale bar 200 µm. FIG. 1(f) shows quantitation of fluorescence of paired FFPE normal and colorectal cancer specimens (n=24). Paired t-test (**$p<0.0001$).

FIG. 3(a) illustrates an FFPE section of colonic epithelium from a patient with familial adenomatous polyposis (FAP) showing low grade dysplasia in an early polyp, surrounded by histologically normal epithelium. WFA-fluorescein (green), MUC2A (red) and DAPI (blue). ×5 objective. The level of WFA binding and MUC2 protein expression are both severely reduced even in early adenomatous polyps. Scale bar 200 µm. H+E image, ×5 objective. See FIG. 17(b) for quantitation of fluorescence, n=5. FIG. 3(b) comprises representative images of FFPE sections from wild-type ileum and colon, and normal ileum and ileal polyp from Min mice (Apc-min/+) stained with WFA-fluorescein. DAPI (blue) and WFA-fluorescein (green) ×20 objective. Scale bar 200 µm. H+E images, ×20 objective. See FIG. 17(c) for quantitation of fluorescence, n=5. FIG. 3(c) comprises representative images of FFPE sections of ileum, proximal colon, and distal colon from both wild-type and Muc2−/− mice, stained with DAPI (blue) and WFA-fluorescein (green) ×20 objective. WFA binding to intestinal epithelium is reduced in Muc2−/− mice compared to wild-type. Scale bar 200 µm. H+E images, ×20 objective. See FIG. 17(d) for quantitation of fluorescence, n=5

FIG. 4 includes examples of images of FFPE sections of specimens from patients with ulcerative colitis, stained with DAPI (blue), MUC2A (red) and WFA-fluorescein (green) ×5 objective. All examples are from patients with ulcerative colitis. Top panel shows active, inflamed tissue with no dysplasia. Middle panel shows ulcerative colitis with low-grade dysplasia (LGD). Bottom panel shows ulcerative colitis with cancer (CA). H+E images, ×4 objective. Quantitation of fluorescence of further examples is shown in FIG. 17(e), n=5 in each group.

FIG. 6(a) shows representative white light (top panel) and IVIS 200 fluorescence images (middle panel) of fresh paired normal mucosa and cancer incisional biopsies from the rectosigmoid, labelled with WFA-fluorescein 1:200, 10 minutes at 37° C. White scale bar equals 2 cm. Colour scale (top right) indicates fluorescence intensity. H+E stained sections (bottom panel) from imaged specimens ×4 objective. Black scale bar equals 200 µm. FIG. 6(b) shows quantitation of fluorescence of fresh paired normal and colorectal cancer specimens imaged using the IVIS 200 camera after application of WFA-fluorescein (n=12) for 10 minutes at 37° C. Paired t-test (***p<0.001) The average normal to cancer fluorescence ratio is 2.5.

FIG. 7(a) shows a white light image of a specimen opened up longitudinally. Rectosigmoid cancer highlighted by dashed line. The adjacent mucosa macroscopically normal. Blue bar=10 cm. FIG. 7(b) shows a fluorescent image of a specimen acquired using IVIS 200 camera, after application of WFA-fluorescein for 10 minutes at 37° C. then washing briefly twice. FIG. 7(c) shows the histology of sections indicated in (b) ×4 objective. Black scale bar equals 200 µm.

FIG. 8(a) shows white light image of total colectomy specimen from a patient with chronic ulcerative colitis, DALM formation and distal sparing disease, opened up longitudinally. Conventional colonoscopy was able to identify the large DALM area in the mid-transverse colon prior to resection (large arrow, encircled by dashed line), but did not detect the small DALM area more proximally (small arrow, encircled by dashed line), as demonstrated by fluorescent WFA. Blue dashed line represents an area of the specimen without mucosa. Blue bar=10 cm. FIG. 8(b) shows a fluorescent image of a specimen acquired using IVIS 200 camera, after application of WFA-fluorescein for 10 minutes at 37° C. then washing briefly twice, overlaid on a grey-scale image and grid, allowing correlation of WFA fluorescence with histology. FIG. 8(c) shows a fluorescent image of specimen with intensity scale bar. FIG. 8(d) shows histology of tissue mapped to the grid shown in (b), demonstrating non-inflamed tissue (grid E4), inflamed tissue (grid H3), large DALM (grid D2) and a more subtle area of DALM that was not apparent during white light endoscopy (grid B6). ×4 objective Black scale bar equals 200 µm.

FIG. 9(a) shows a white light image of a TEMS specimen from a patient with rectal cancer recurrence following previous polypectomy and radiotherapy. Black bar=5 cm. FIG. 9(b) is a fluorescent image of a specimen acquired using IVIS 200 camera, after application with WFA-fluorescein for 10 minutes at 37° C. then washed briefly twice. Image overlaid by grid, allowing correlation of WFA fluorescence with histology. FIG. 9(c) is a grey scale image of a specimen. FIG. 9(d) is a fluorescent image of a specimen with intensity scale bar. FIG. 9(e) illustrates the histology of tissue mapped to the grid shown in FIG. 9(b), demonstrating areas of non-dysplastic tissue (Grids G1, G2 and D3, ×4 objective), low grade dysplasia (Grid C3, ×4 objective) and an area that was previously biopsied, with denuded epithelium, fibrosis (F) and underlying recurrent rectal cancer (CA) (Grid C2, ×2 objective). Black scale bar equals 200 µm. Red scale bar equals 400 µm.

FIG. 10(a) is a white light image (left) and fluorescence image (middle) of an anterior resection specimen. White scale bar 1 cm. Non-dysplastic (ND) tissue is bright, compared to the cancer (CA), encircled in dashed line. Histology ×4 objective (right) Black bar 200 μm. FIG. 10(*b*) is a white light image (left) and fluorescence image (middle) of a TEMS specimen with overlying grid to correlate with histology (right) ×4 objective. White bar 5 cm. Black bar 200 μm Box 3 is non-dysplastic tissue with the brightest fluorescence. Box 2 is invasive cancer and correlates with the darkest area of fluorescence. Box 1 has an intermediate level of fluorescence, and is histologically high-grade dysplasia (HGD). FIG. 10(*c*) is a white light image (left) and fluorescence image (middle) of anterior resection specimen from a patient with multiple left-sided polyps. White scale bar 1 cm. Due to the size of this sample, the imaging system was used in wide-field mode. All polyps sampled (samples 1-5) were tubular adenomas (TA), and these polyps were of much lower fluorescence compared to the non-dysplastic tissue (sample 6). Histology ×4 objective (right). Black bar 200 μm FIG. 10(*d*) is a white light image (left) and fluorescence image (middle) of an anterior resection specimen. White scale bar 1 cm. This specimen was imaged under insufflation in conditions simulating colonoscopy. There were two cancer lesions in this specimen, one that was visible on white light endoscopy (CA1, red arrow) and another flat lesion that was not apparent under white light visualization (CA2, encircled in blue) but had low WFA-Cy5 fluorescence. ND=non-dysplastic. Histology ×4 objective (right). Black bar 200 μm.

FIG. 13—shows the results of competitive binding assays and demonstrates that with increasing concentrations of free N-acetylgalatosamine (GalNAc), there is reduced binding of WFA, demonstrating specificity of WFA to free GalNAc residues on the tissue specimen. DAPI (blue) and WFA-fluorescein (green), ×5 objective, Scale bar 200 μm. Bottom panel—quantification of fluorescence of WFA, n=5.

Figure 2:
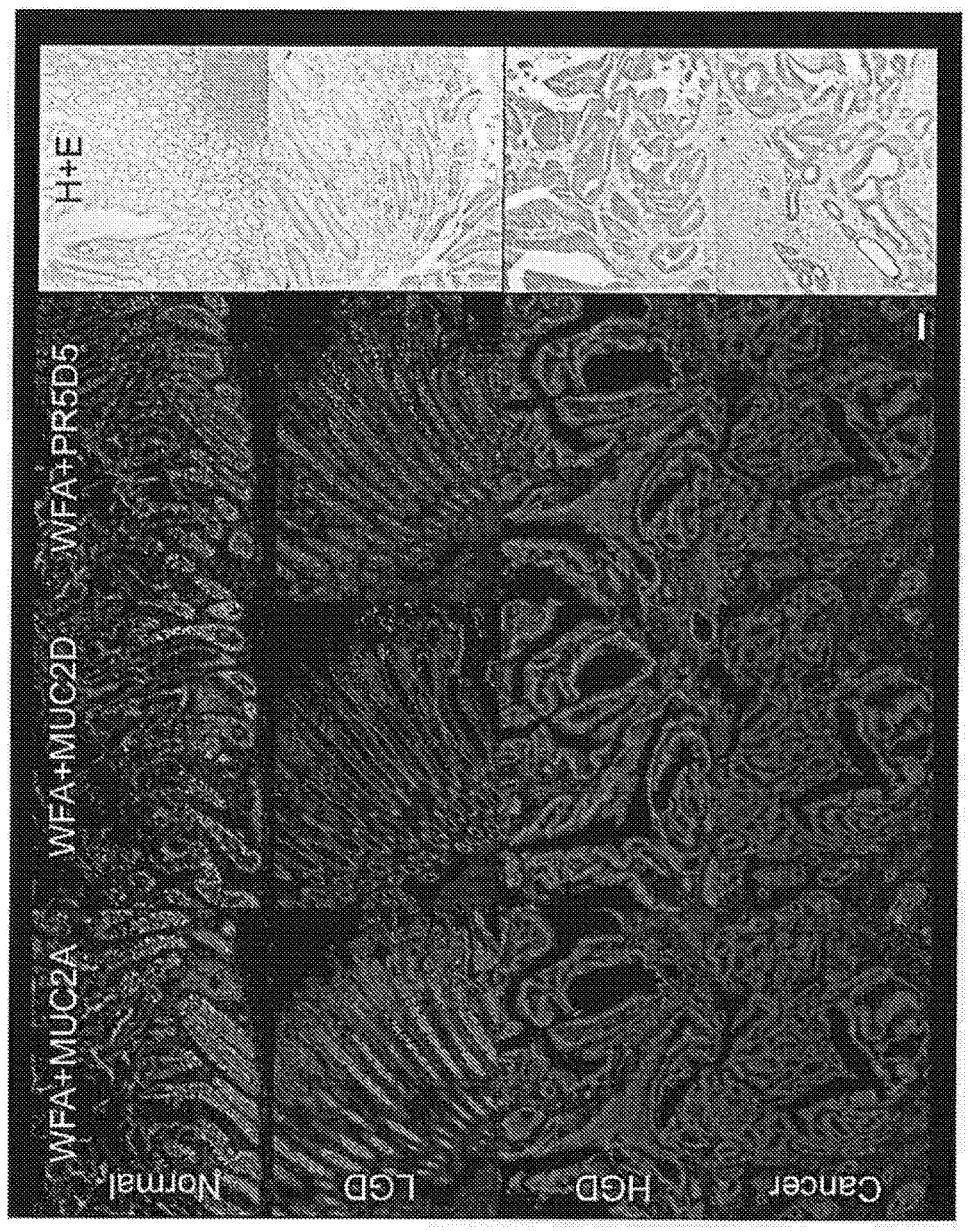
FIG. 2—shows that WFA binds to mature forms of MUC2. Representative immunofluorescence FFPE serial sections of normal human colonic epithelium, low-grade dysplasia (LGD), high-grade dysplasia (HGD) and cancer stained with DAPI (blue), WFA-fluorescein (green), and either MUC2A (left, red), MUC2D (middle, red) or PR5D5 (right, red) ×5 objective. Scale bar 200 µm. H+E images ×4 objective. Enlarged images of top panel, detailing the staining of the colonic epithelial crypts are shown in FIG. 15. Quantitation of fluorescence of further examples is shown in FIG. 17a, n=5 in each group. WFA does not bind to MUC2 positive cells at the base of the crypt, but binds increasingly to goblet cells higher in the crypts, and strongly to secreted mucus, suggesting that WFA binds to mature and possibly also the more but not completely mature, glycosylated forms of MUC2. Note the reduction of WFA binding to LGD, in the presence of MUC2 expression, suggesting that early changes in glycosylation are responsible for the reduced WFA binding in LGD as opposed to changes in MUC2 protein expression. In HGD and cancer specimens, both WFA binding and MUC2 protein expression are lost.
Figure 3:
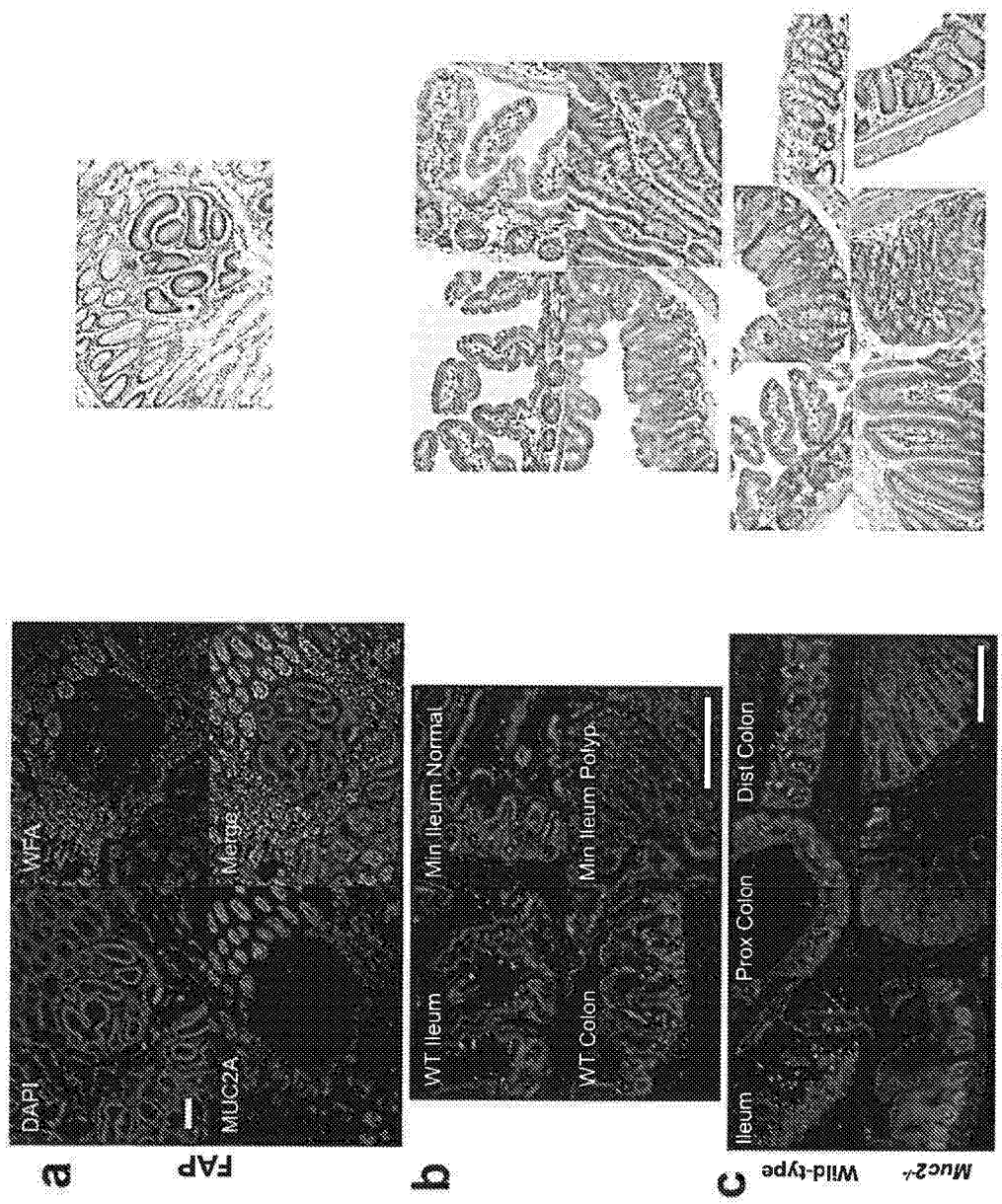
FIG. 3—illustrates WFA staining on adenomas from FAP patients and the ApcMin mouse.
Figure 4:
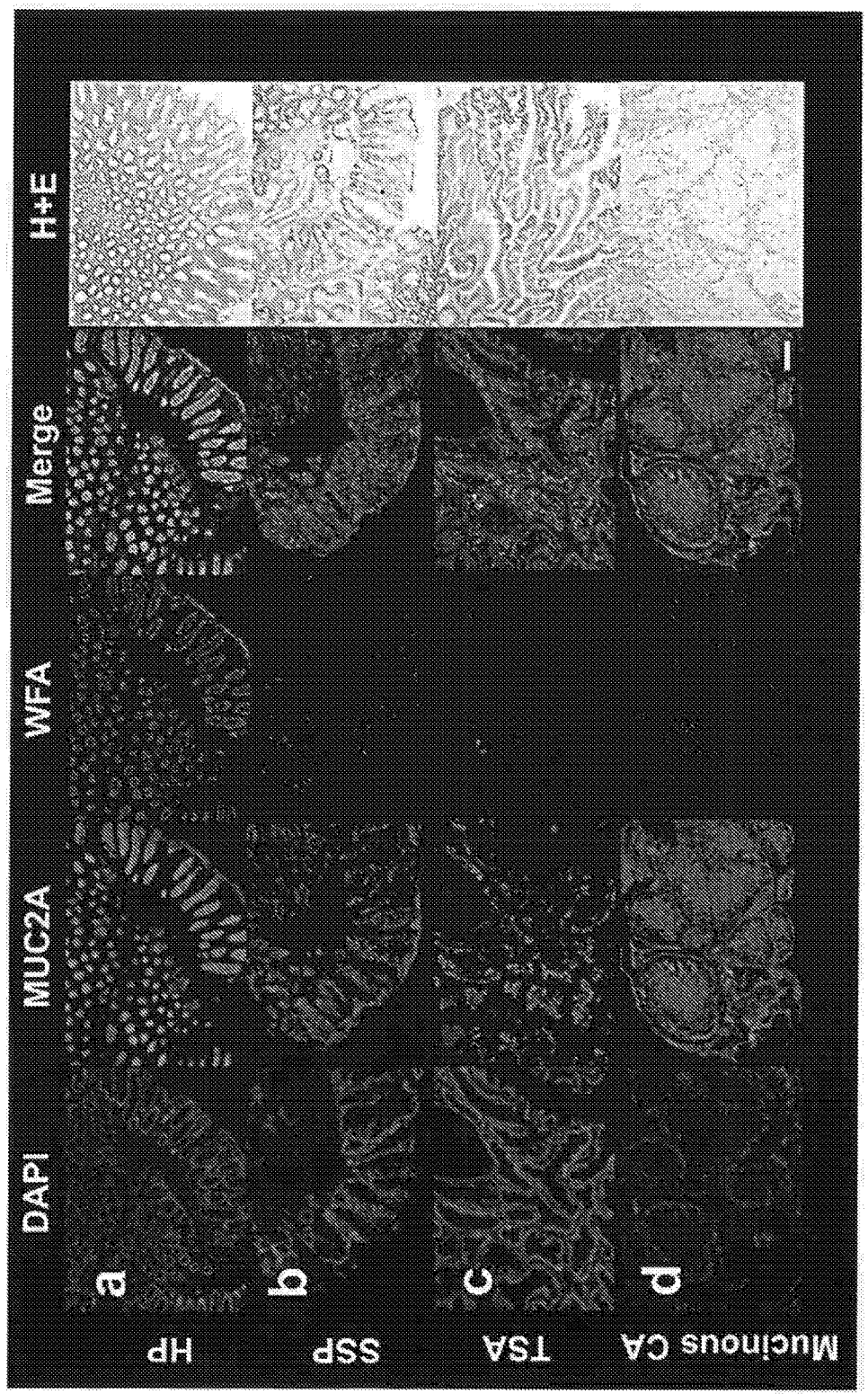
FIG. 4—shows WFA and MUC2 immunofluorescence of UC FFPE specimens.
Figure 5:
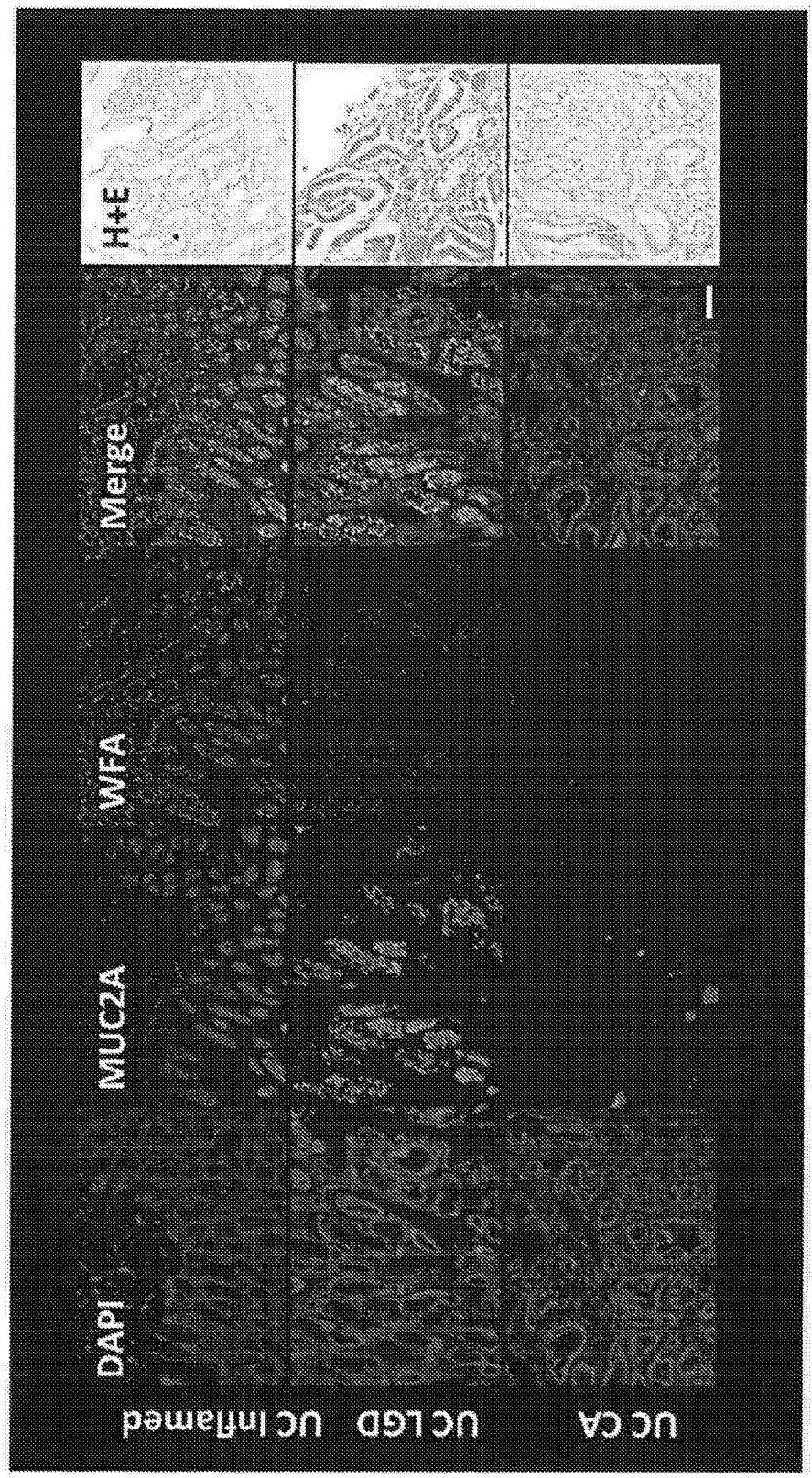
FIG. 5—demonstrates that WFA binds to mucin produced by hyperplastic polyps but not to mucin produced by sessile serrated polyps, traditional serrated polyps and mucinous cancers. Representative immunofluorescence FFPE serial sections of human (A) hyperplastic polyp (HP), (B) sessile serrated polyp (SSP), (C) traditional serrated adenoma (TSA) and (D) mucinous carcinoma (CA) are shown. Stained with DAPI (blue), WFA-fluorescein (green), and MUC2A (red) ×5 objective. H+E images, ×4 objective. Quantitation of fluorescence of further examples is shown in FIG. 17(f), n=5 in each group.

(a) Relates to FIG. 2—Normal, LGD, HGD and cancer tissue, unpaired t-test
(b) Relates to FIG. 3*a*—FAP normal versus FAP small polyp, paired t-test
(c) Relates to FIG. 3*b*—wild-type ileum and colon, and normal ileum and ileal polyp from Min mice (Apcmin/+), paired t-test
(d) Relates to FIG. 3*c*—ileum, proximal colon and distal colon from both wild-type and Muc2−/− mice, unpaired t-test
(e) Relates to FIG. 4—ulcerative colitis with inflammation, LGD and cancer, unpaired t-test
(f) Relates to FIG. 5—hyperplastic polyp (HP), sessile serrated polyp (SSP), traditional serrated adenoma (TSA) and mucinous carcinoma (CA), unpaired t-test.

Figure 18:
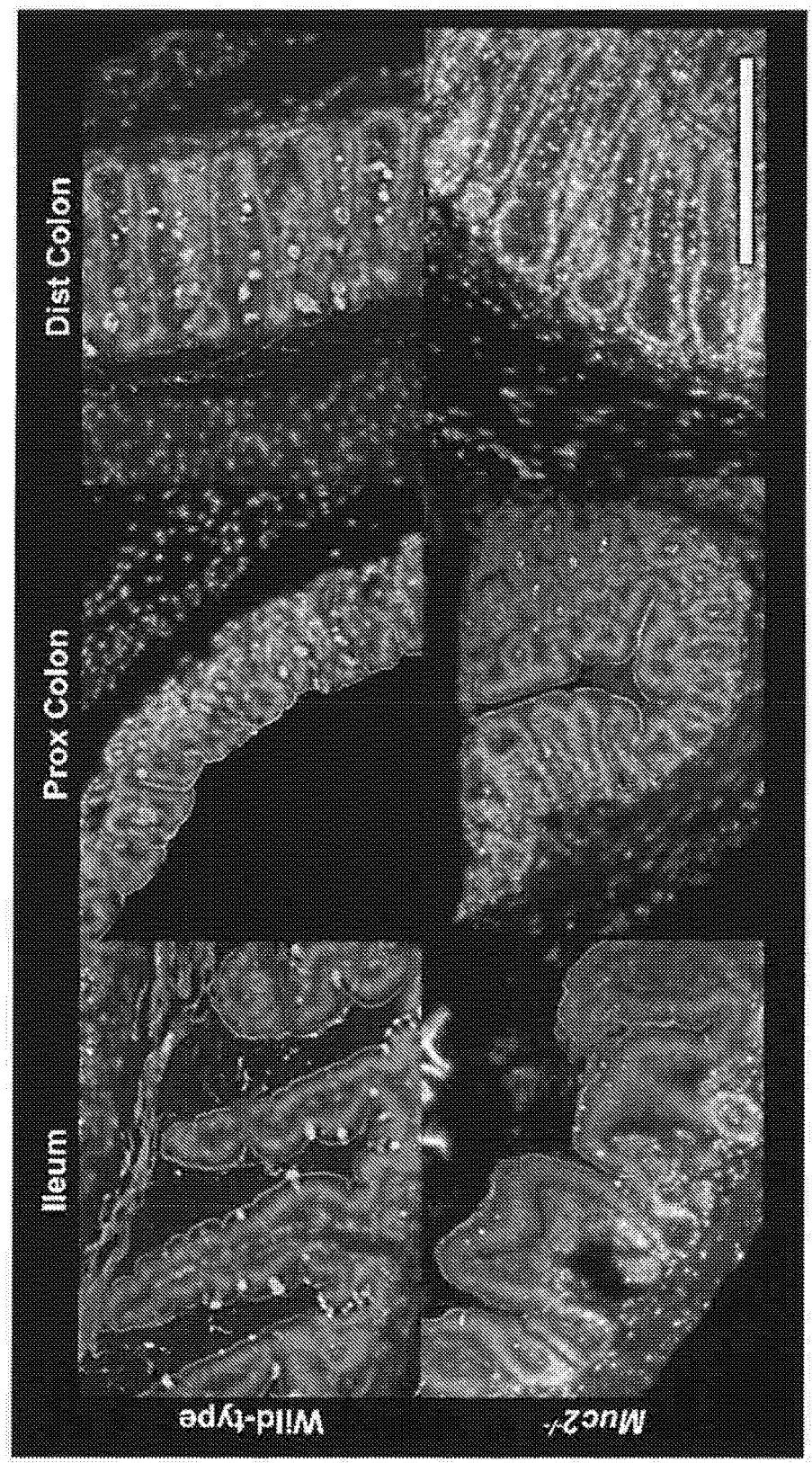

FIG. 18—shows further examples of images of FFPE sections of ileum, proximal colon, and distal colon from both wild-type and Muc2−/− mice, stained with DAPI (blue) and WFA-fluorescein (green) ×20 objective. Scale bar 200 μm.

Figure 19:
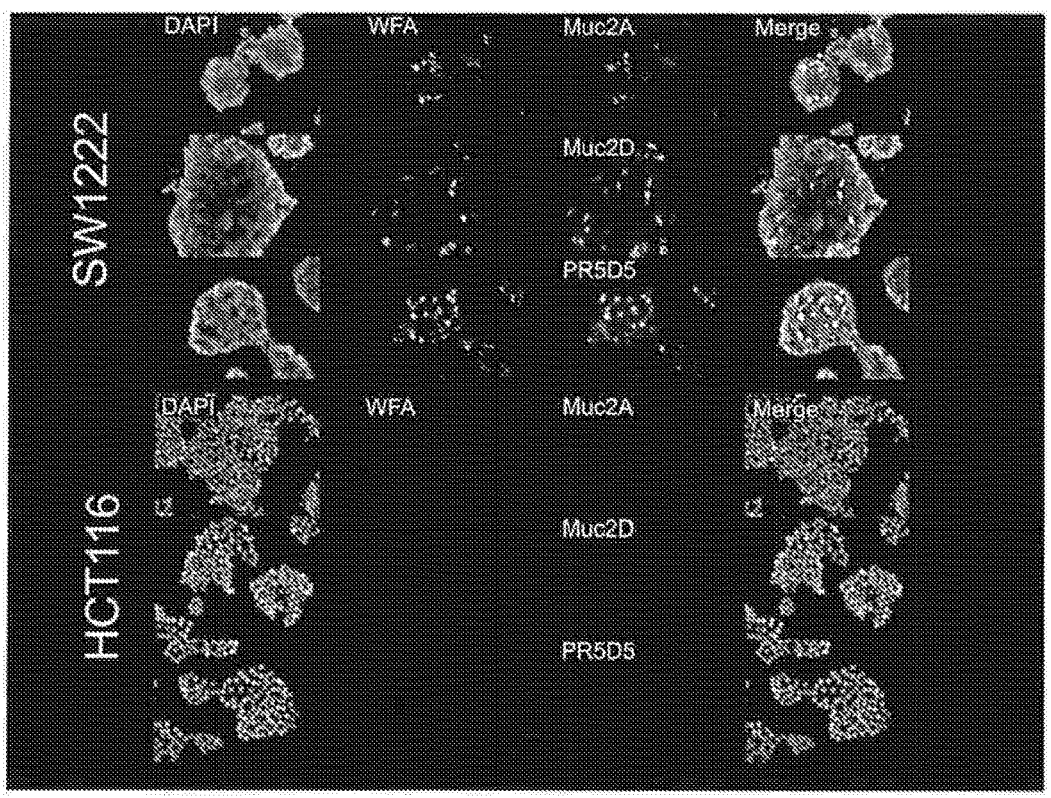

FIG. 19—shows images of SW1222 and HCT116 cell lines, stained with WFA-fluorescein (green), Muc2A/Muc2D/PR5D5 (red) and DAPI (blue) ×5 objective. SW1222 can differentiate into all three epithelial lineages, including goblet cells that label with WFA and which co-localises with Muc2 and PR5D5 staining. HCT116 is a cell line with a high proportion of cancer stem cells and does not differentiate to form goblet cells. None of Muc2A, Muc2D, PR5D5 or WFA bind to HCT116, which is consistent with the fact that this cell line does not express Muc2 and does not produce goblet cells.

Figure 20:
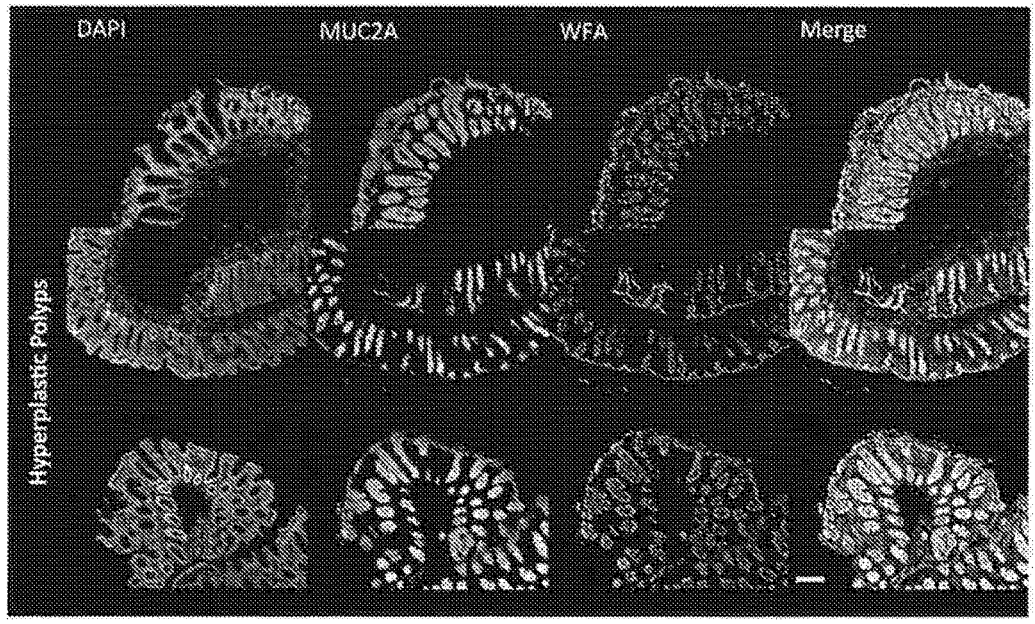

FIG. 20—shows further examples of images of FFPE sections of 3 separate hyperplastic polyp specimens, stained with DAPI (blue), MUC2A (red) and WFA-fluorescein (green) ×5 objective. Scale bar 200 μm.

Figure 21:
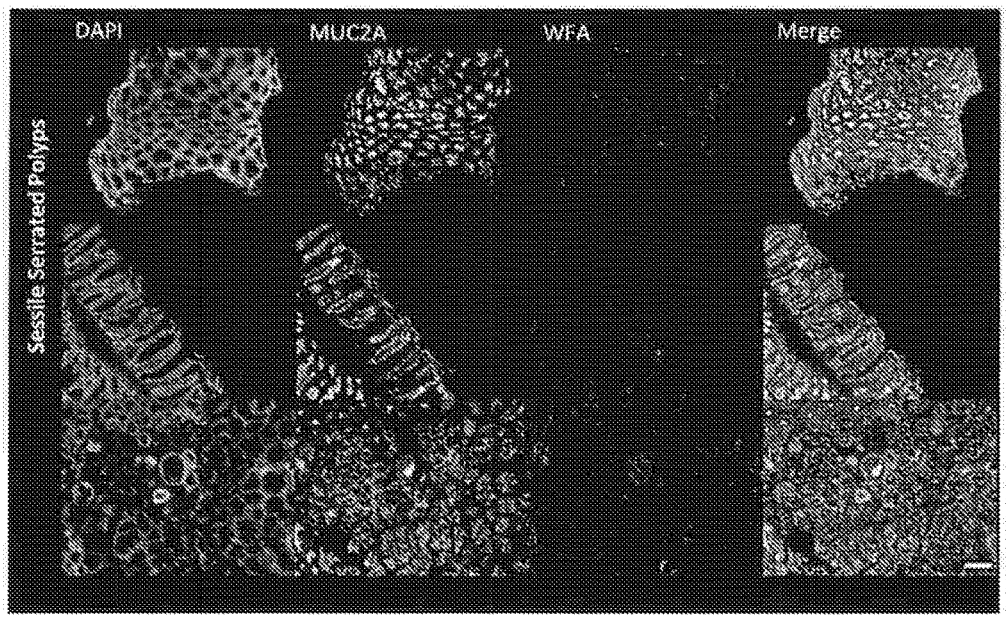

FIG. 21—shows further examples of images of FFPE sections of 3 separate sessile serrated polyp specimens, stained with DAPI (blue), MUC2A (red) and WFA-fluorescein (green) ×5 objective. Scale bar 200 μm.

Figure 22:
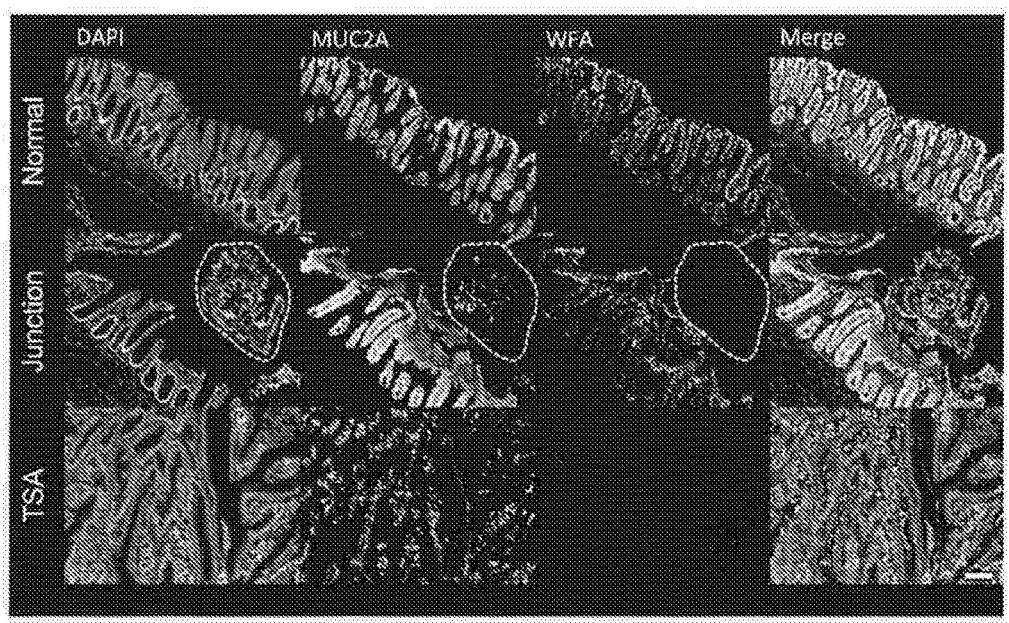

FIG. 22—shows further example of images of FFPE sections from a traditional serrated adenoma specimen (bottom panel) stained with DAPI (blue), MUC2A (red) and WFA-fluorescein (green) ×5 objective. Normal epithelium from the same patient is shown on the top panel. The junction where normal epithelium transitions to TSA is shown in the middle panel, with the TSA highlighted by a dashed white line. Scale bar 200 μm.

Figure 23:
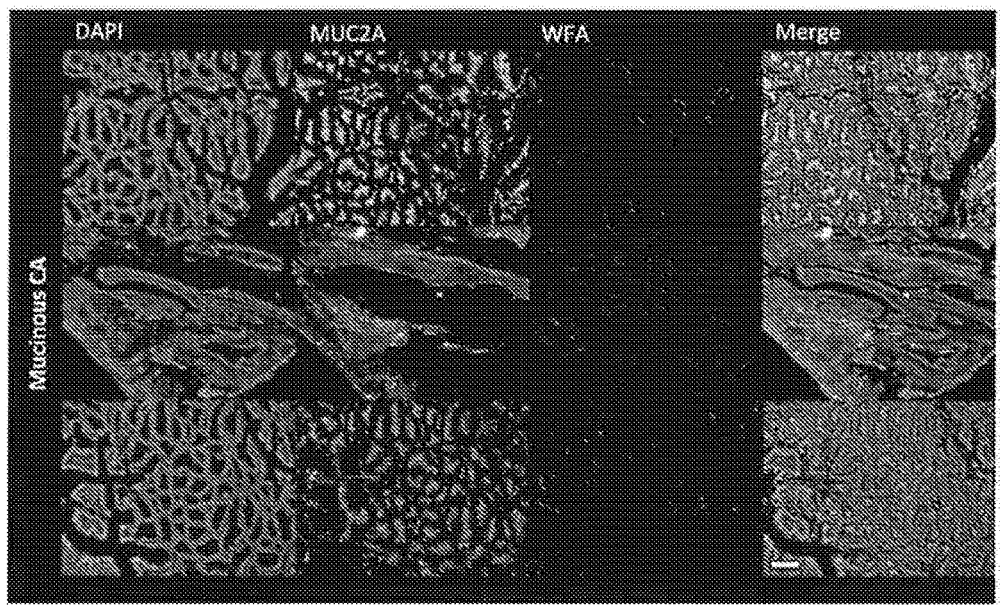
Figure 24:
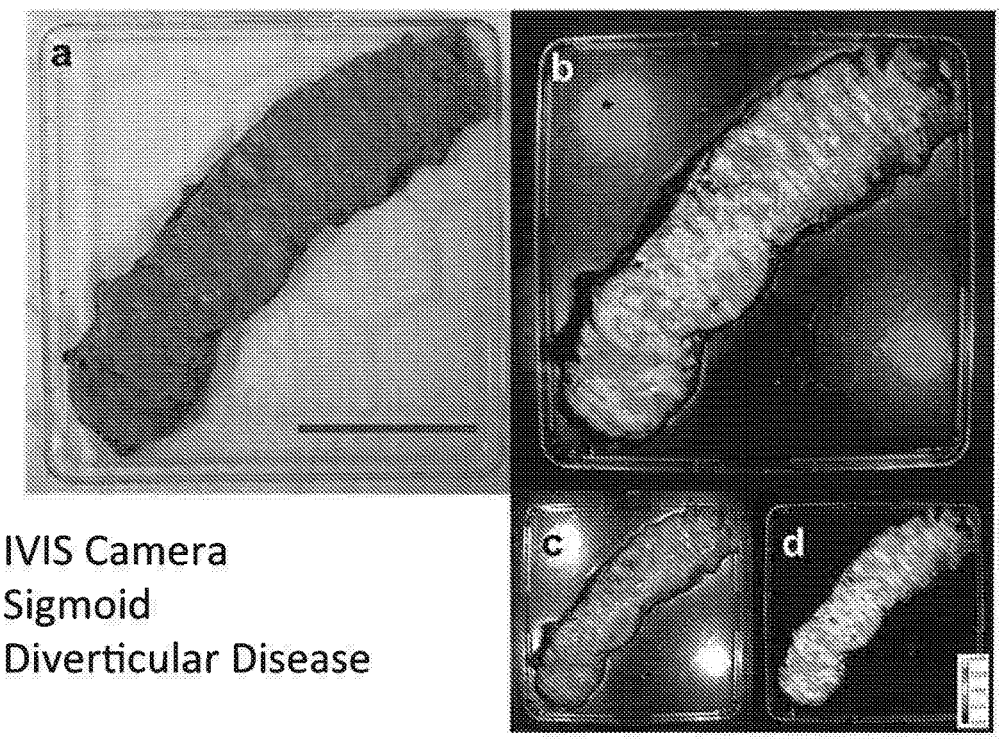

FIG. 23—shows further examples of images of FFPE sections of 3 separate mucinous cancer specimens, stained with DAPI (blue), MUC2A (red) and WFA-fluorescein (green) ×5 objective. Scale bar 200 μm FIG. 24—is a validation of fluorescent WFA using whole organ fresh tissue: sigmoid colectomy for diverticular disease. FIG. 24(*a*) shows a white light image of a specimen opened up longitudinally. This specimen contained multiple diverticulae, but did not contain any dysplastic lesions and therefore served as a negative control. Blue scale bar 10 cm. FIG. 24(*b*) shows a fluorescent image of s specimen acquired using IVIS 200 camera, after application of WFA-fluorescein for 10 minutes at 37° C. and then washing briefly twice. Image superimposed onto a grey-scale image of specimen. FIG. 24(c) is grey-scale image of the specimen. FIG. 24(d) is a fluorescent image of the specimen with intensity scale bar.

FIG. 25—is a quantitation of fluorescent imaging of resected whole colorectal specimens labelled with WFA-fluorescein using the IVIS 200 camera. Based on differential levels of fluorescence, regions of interest were identified for further histological analysis. ^ Normal to cancer fluorescence ratio was calculated for samples 1, 2 and 3. Normal to dysplasia fluorescence ratio was calculated for sample 4. Mean ratio=2.6. No CA/dysplasia in sample 5 to do ratio calculation ^^ normal colonic mucosa for sample 4 is distal spared colonic mucosa on background of UC.

Figure 26:
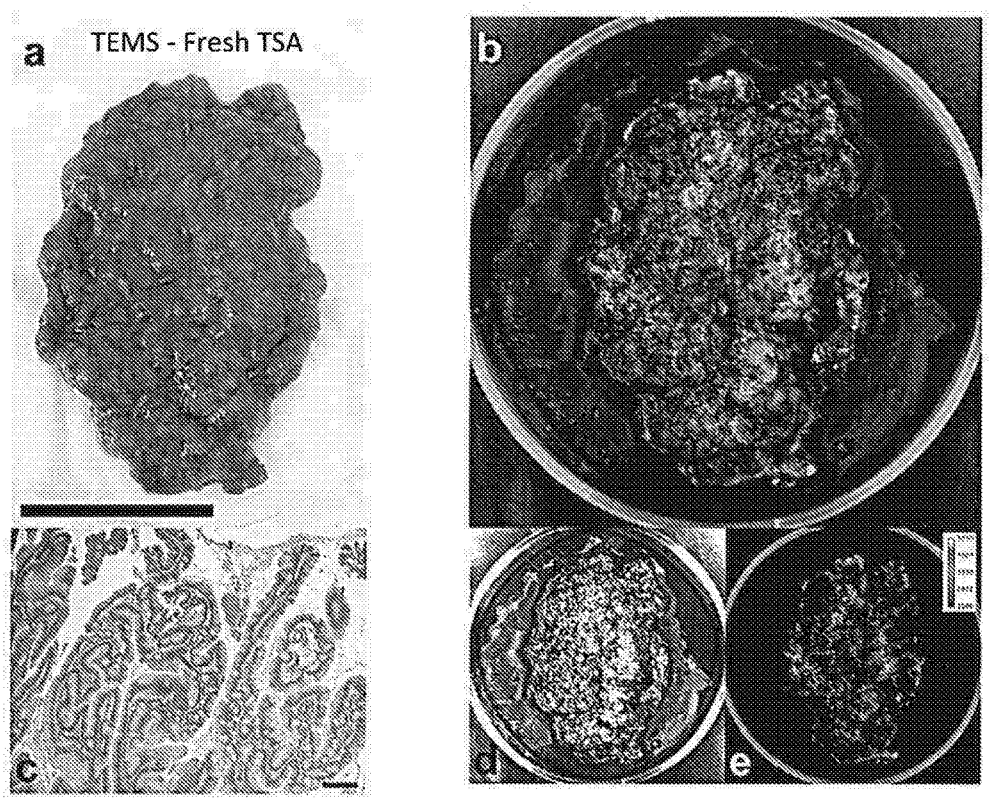

FIG. 26—shows in FIG. 26(a) a white light image of a freshly resected traditional serrated adenoma (TSA). Black bar=5 cm. FIG. 26(b) shows a fluorescent image of a specimen acquired using IVIS 200 camera, after application of WFA-fluorescein for 10 minutes at 37° C. and then washing briefly twice. Image superimposed onto a grey-scale image of specimen. FIG. 26(c) is an H+E section of a specimen confirming diagnosis of TSA, ×4 objective. Scale bar 200 µm. FIG. 26(d) is a grey-scale image of a specimen and FIG. 26(e) is a fluorescent image of specimen with intensity scale bar.

Figure 27:

FIG. 27—shows images of normal colonic epithelium (FFPE) co-stained with fluorescent WFA-fluorescein and WFA-Cy5, DAPI blue). ×5 objective, demonstrating good co-localisation of both labeling agents and confirming that conjugating WFA with Cy5 did not alter its binding specificity. Scale bar 200 µm.

Figure 28:
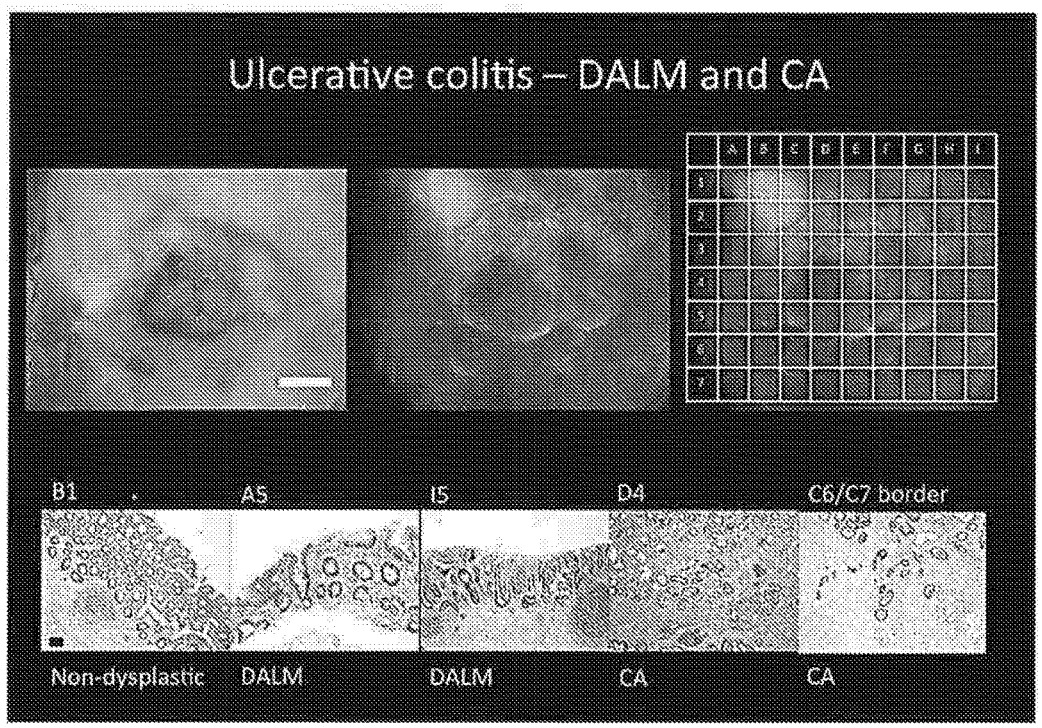

FIG. 28—shows in the top panel: white light image (left) and fluorescence image (middle) of an anterior resection specimen from a patient with ulcerative colitis and DALM, after application with WFA-Cy5. White scale bar 1 cm. Grid superimposed on fluorescence image (right). WFA-Cy5 was able to distinguish a flat area of dysplasia (Grid A5) from non-dysplastic tissue (Grid B1), even though this was not obvious on white light endoscopy. This specimen also had two areas of invasive CA, in Grid D4 and at the border of C6/C7. Histology ×4 objective (lower panel) Black bar 200 µm.

Figure 29:
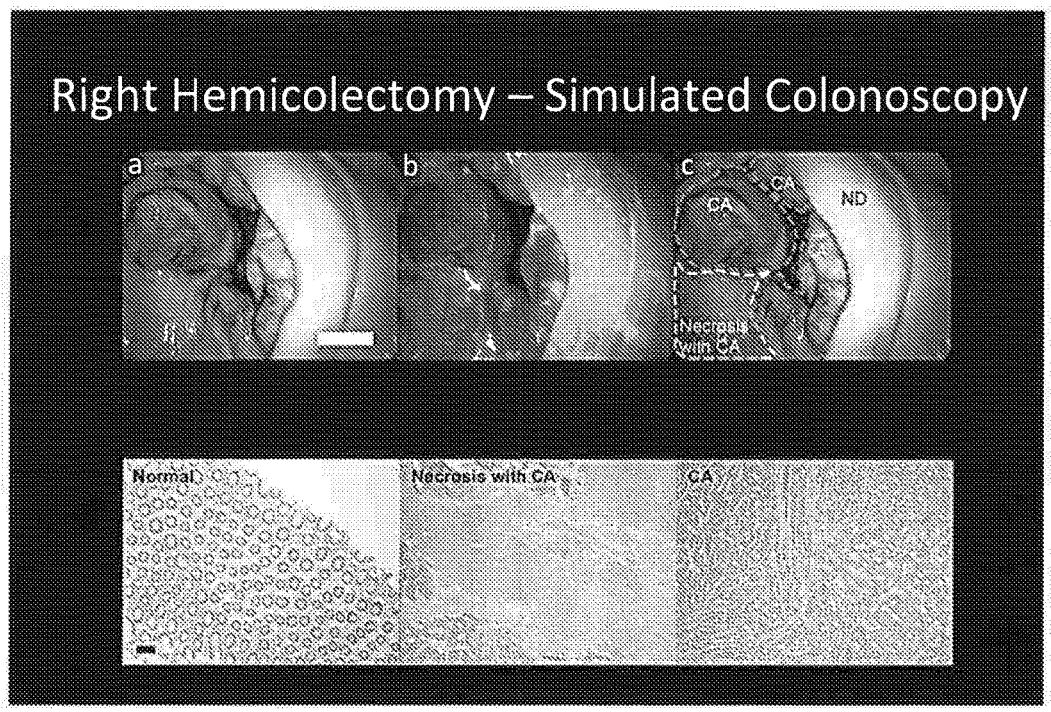

FIG. 29—shows in FIG. 29(a) a white light image and in FIG. 29(b) a fluorescence image of a right hemicolectomy specimen after application with WFA-Cy5. White scale bar 1 cm. This specimen was imaged under insufflation in conditions simulating colonoscopy. The dark area of fluorescence correlates with cancer (CA), encircled in red lines FIG. 29(c). There is also an area of necrosis with cancer, encircled in a blue line that is not readily seen using white light endoscopy alone, but is highlighted by low fluorescence. Histology ×4 objective (lower panel) Black bar 200 µm.

FIG. 30—shows the quantitation of fluorescent imaging of resected whole colorectal specimens labelled with WFA-fluorescein using the 660 nm fluorescence endoscope system. Specimens 1, 2 and 3 and 5 refer to those shown in FIG. 10. RT=radiotherapy. Normal to cancer fluorescence ratio calculated for samples 1, 2, 4, 5 and 6. Normal to dysplasia ratio calculated for sample 3. Mean ratio=3.6.

Figure 31:
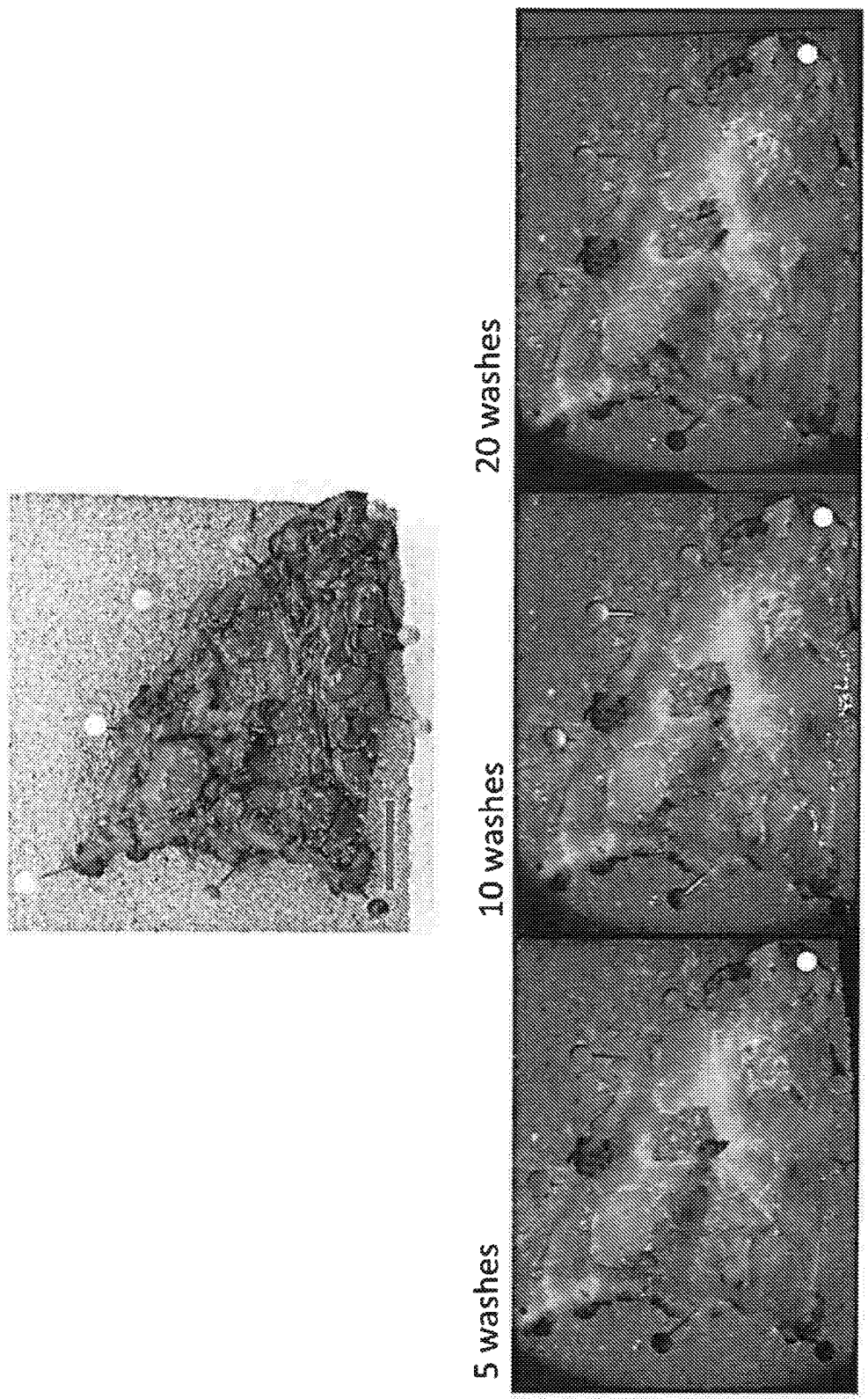

FIG. 31—shows images of a fresh TEMS specimen: white light image and fluorescent image after application with WFA-Cy5 and washed repeatedly. There is a good signal despite multiple washings, confirming that WFA binds tightly to the mucosal surface. Blue scale bar 5 cm.

RESULTS

Figure 1:
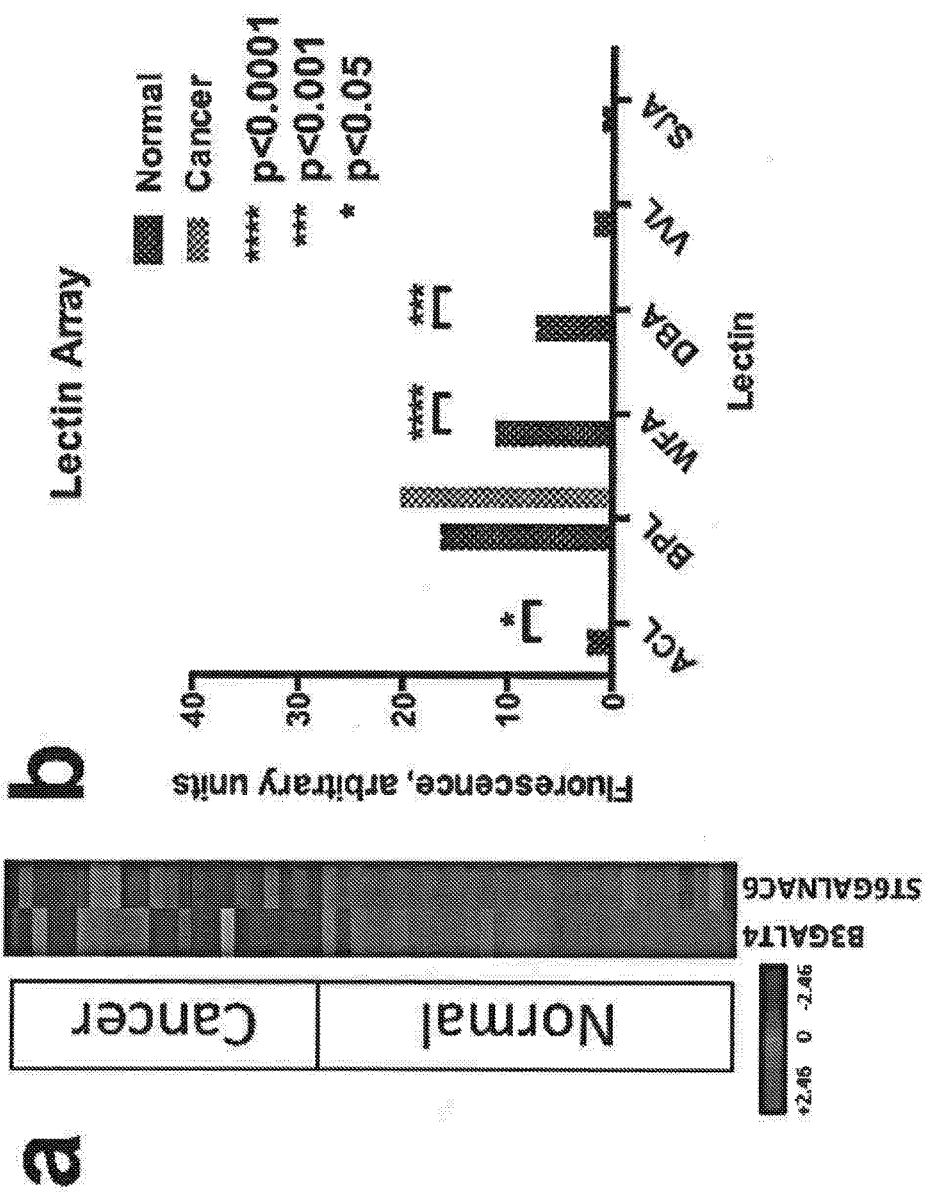
FIG. 1—shows the selection of a fluorescent lectin for use in the invention.
Figure 1:
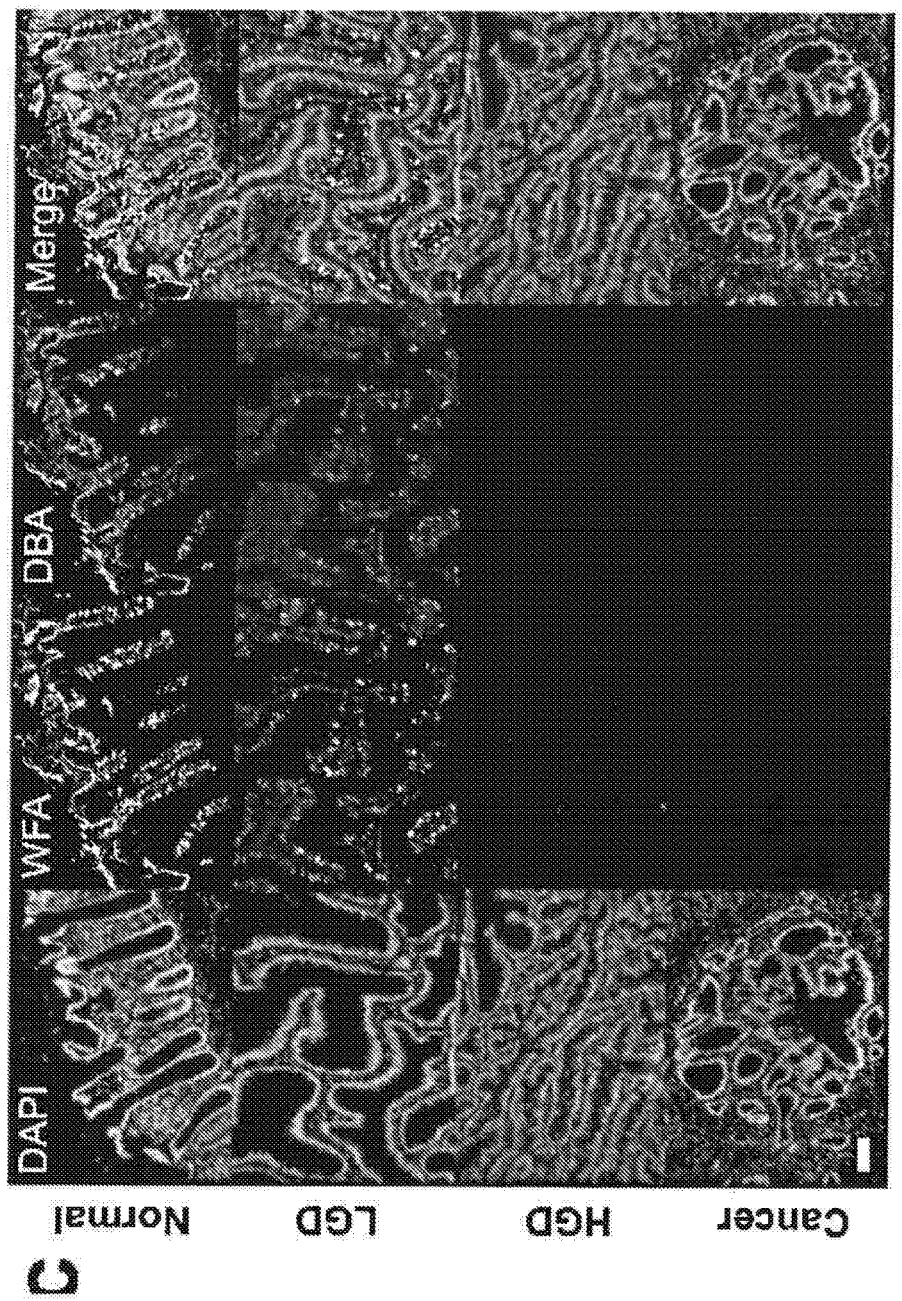
Figure 1:
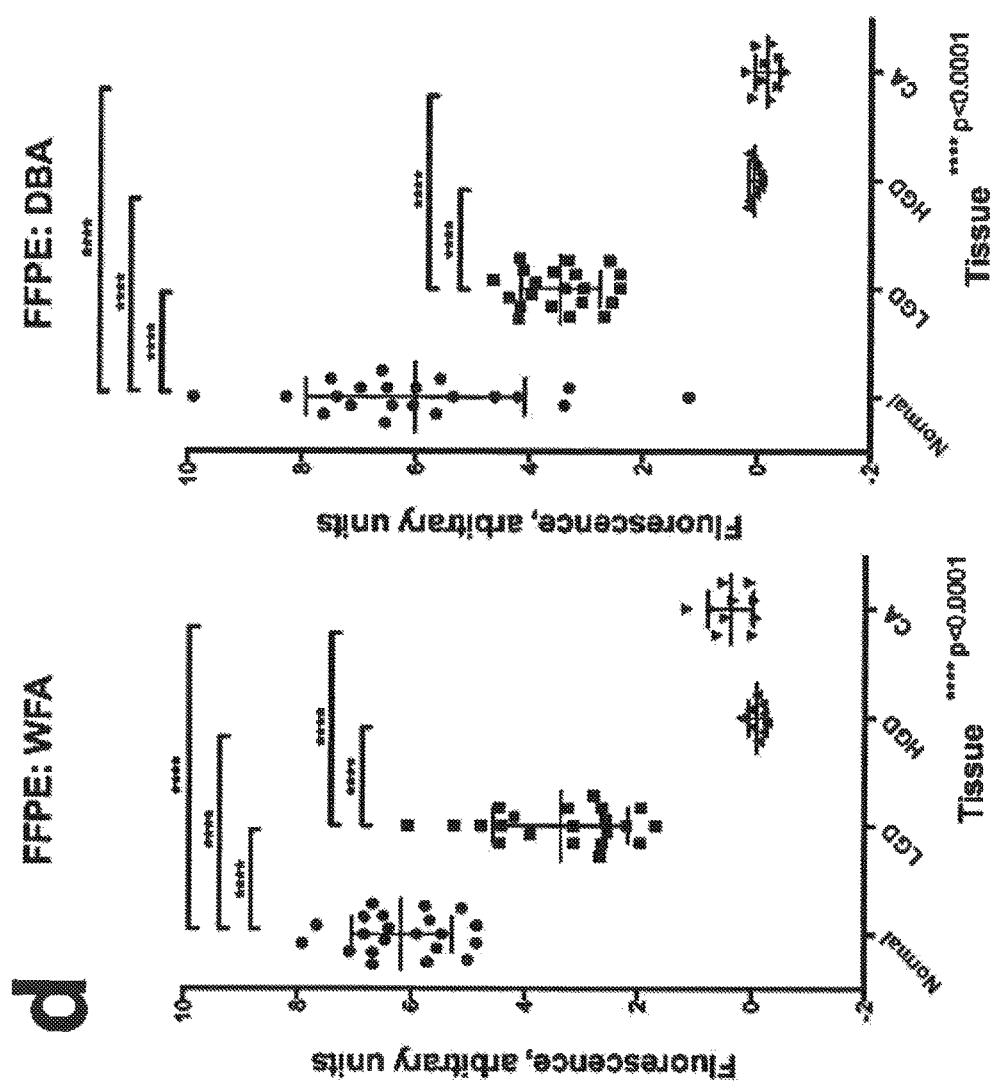
Figure 1:
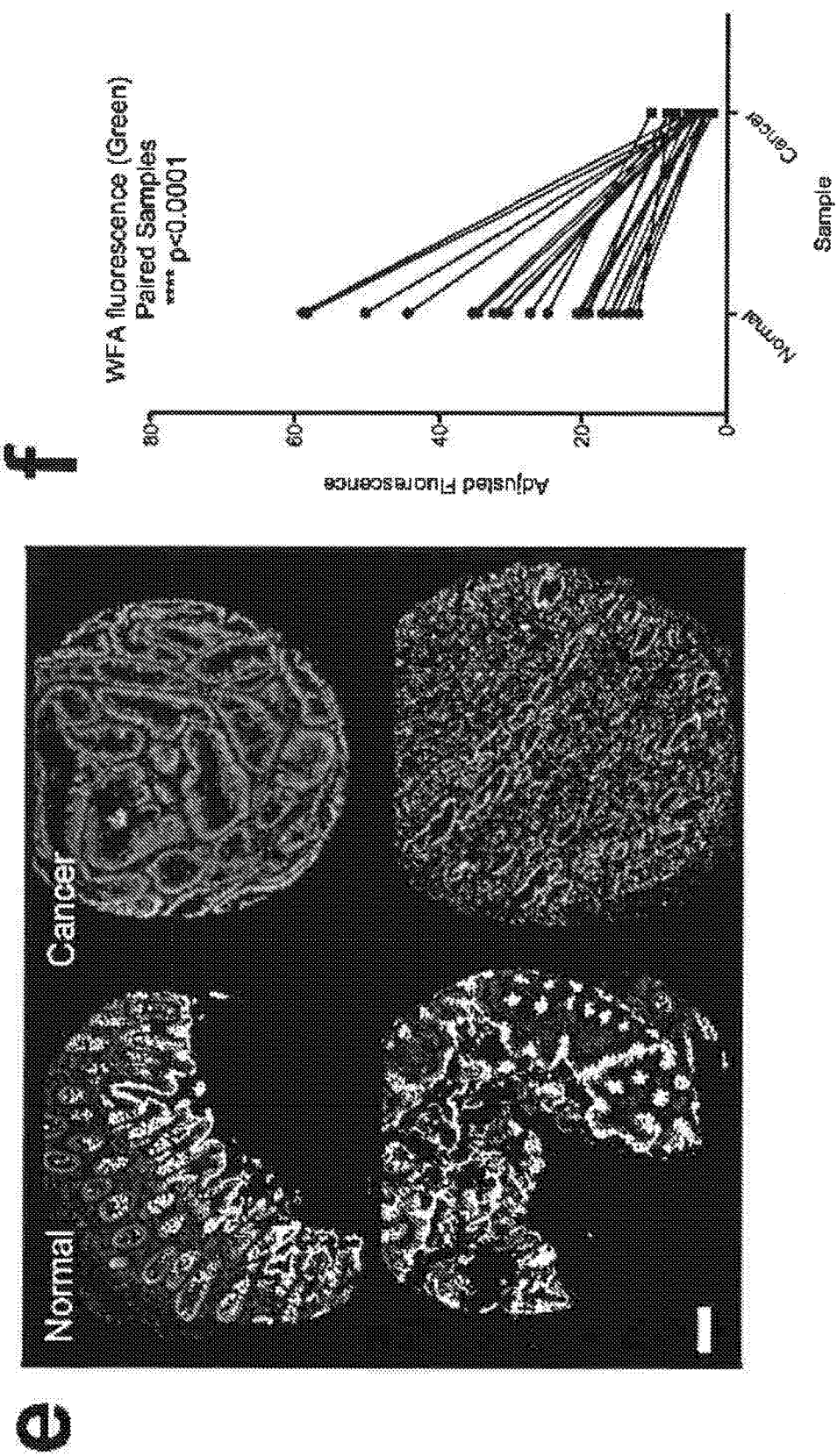
Figure 11:
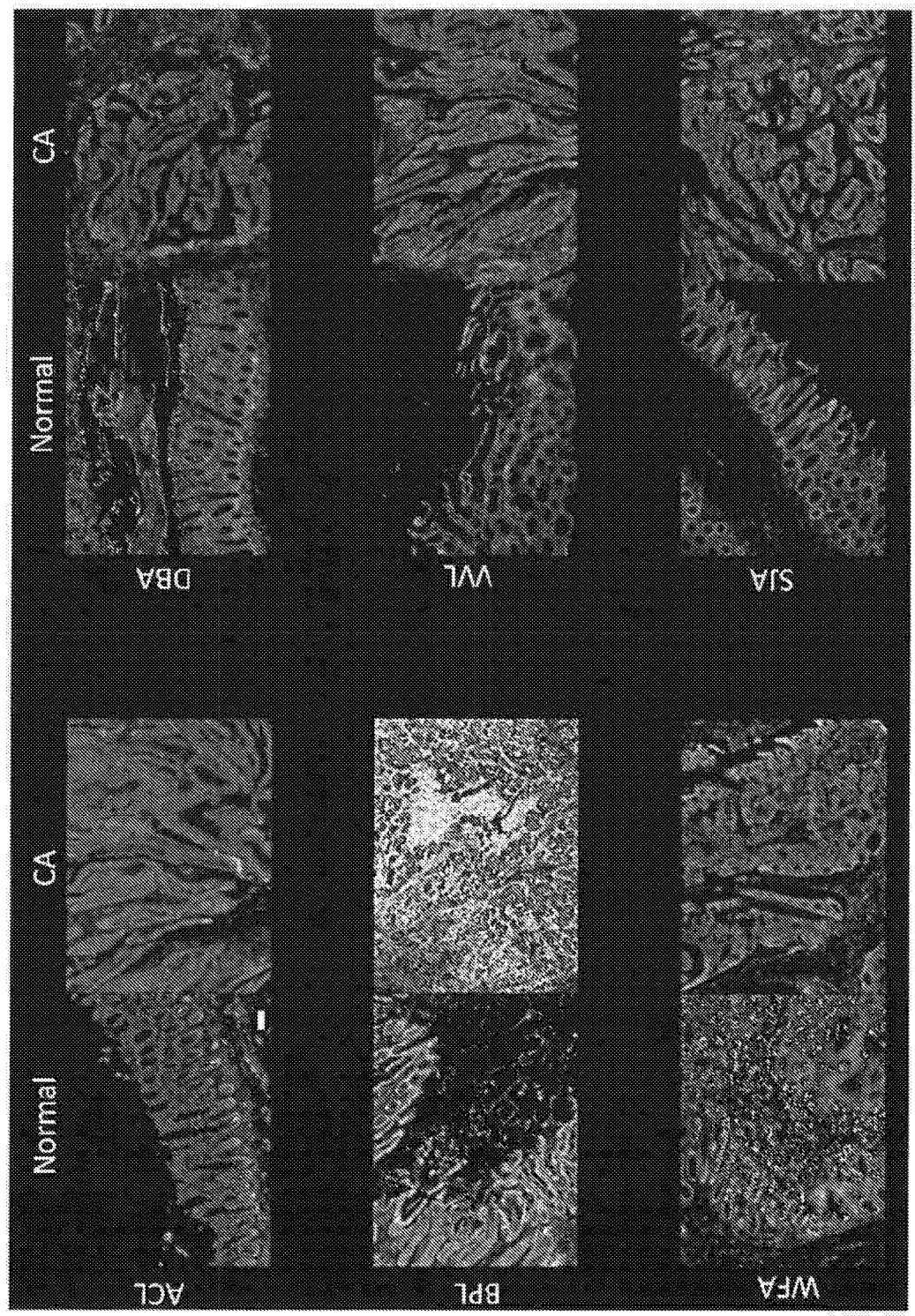
FIG. 11—shows representative images of normal and cancer FFPE specimens stained with fluorescent lectins (ACL-fluorescein, BPL-568, WFA-fluorescein, DBA-568, VVL-Fluorescein, SJA-568, DAPI blue). ×5 objective. Scale bar 200 μm.
Figure 12:
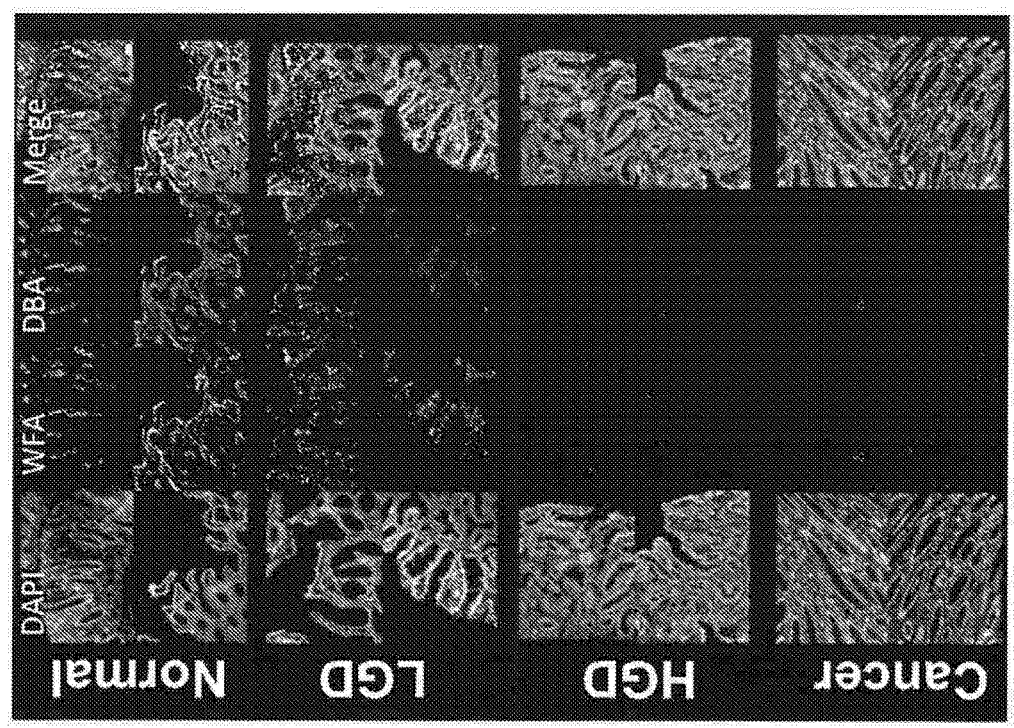
FIG. 12—shows further images of normal, LGD, HGD and invasive colorectal cancer FFPE specimens stained with WFA-Fluorescein and DBA-Rhodamine. ×5 objective Scale bar 200 μm.
Figure 15:
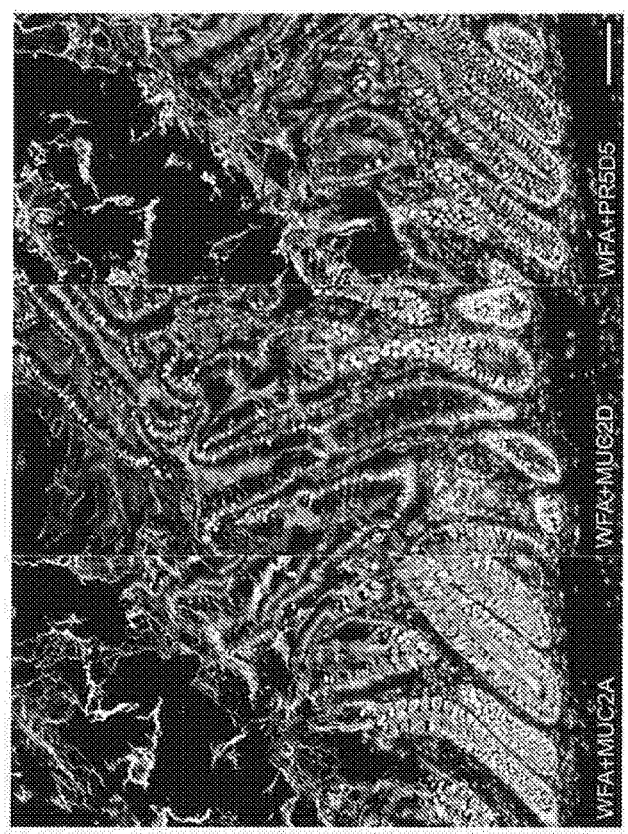
FIG. 15—shows enlarged images of top panel of FIG. 2 top panel. Normal human colonic epithelium WFA-fluorescein (green), and either MUC2A (left, red), MUC2D (middle, red) or PR5D5 (right, red) ×16 objective, scale bar 200 μm. Note that WFA does not bind to goblet cells at the bottom of the crypts, but shows increasing binding to goblet cells they mature. WFA also binds to mucus that has been excreted by goblet cells into the lumen of the crypts.

Selection of Lectins that Bind Differentially to Normal, Dysplastic and Cancer Tissue The mRNA expression levels of a selected set of genes in the glycosphingolipid biosynthetic pathway were compared in 30 colorectal cancer cell lines and 22 normal tissue specimens. The results indicated that the two genes B3GALT4 and ST6GALNAC6 were significantly up regulated in normal tissue compared to colorectal cancer (FIG. 1a). These genes encode a galactosyltransferase and a sialyltransferase respectively, acting on N-Acetylgalactosamine (GalNAc). The lower levels of expression of glycosyltransferases in dysplastic tissue leads to incompletely glycosylated side changes and altered lectin binding The GalNAc binding lectin *Wisteria floribunda* Agglutinin (WFA) is shown herein to be able to distinguish between normal tissue and colorectal cancer. When fluorescently-labeled WFA was exposed to normal and cancer formalin fixed paraffin embedded (FFPE) specimens, WFA and DBA was shown to bind preferentially to the normal tissue (FIG. 1B and FIG. 11). The binding of WFA and DBA on paraffin embedded sections of normal colonic epithelium, low grade dysplasia (LGD), high grade dysplasia (HGD) and cancer is shown in FIG. 1c and FIG. 12. In normal tissue, WFA and DBA appear to co-localise and bind to goblet cells and secreted mucus. There was a successive reduction in binding to colonic epithelium from a cohort of patients with increasing dysplasia, respectively from normal to LGD to HGD and cancer (FIG. 1d).

The ability of fluorescent WFA to distinguish between normal and cancerous tissue was further investigated on paired normal and cancer samples in a colorectal tissue microarray obtained from 24 patients (FIG. 1e). The overall mean fluorescence per position on the microarray was 27.6 units for normal tissue versus 4.8 units for the cancers (paired t-test, $p<0.0001$) (FIG. 1f). Using serial FFPE sections, an increasing concentration of free GalNAc was sufficient to prevent binding of WFA to these tissue sections (FIG. 13) confirming WFA's specificity for GalNAc.

WFA Lectin Binds Mostly to Mature Glycosylated Forms of MUC2

Figure 14:
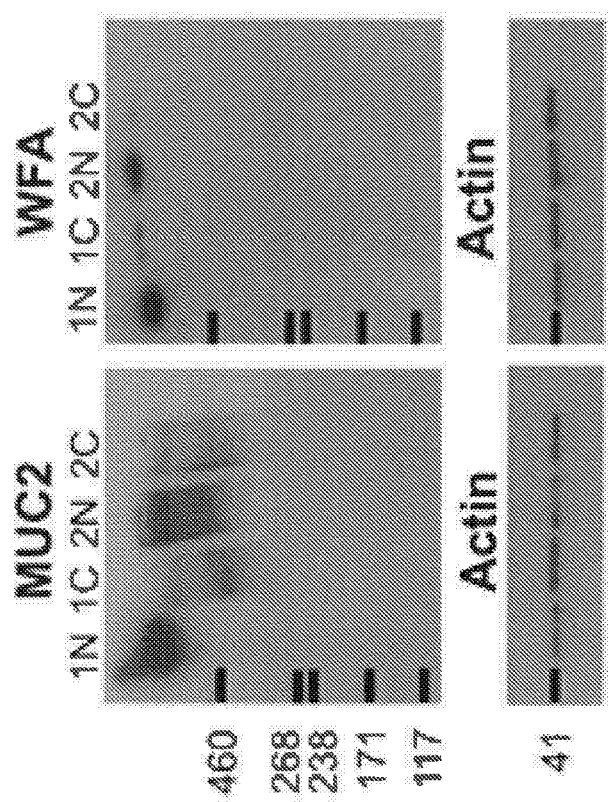
FIG. 14—shows a Western blot with monoclonal anti MUC2 (Muc2D, left) and WFA lectin (right) of paired samples from 2 patients, comparing normal colonic epithelium (N) and colorectal cancer (C). Blots were probed with a monoclonal anti-actin antibody as loading controls. Note that WFA binds to a protein that runs at the same level as MUC2 in the normal tissue, and that both WFA-binding and MUC2 binding levels are significantly reduced in cancer compared to the paired normal tissue.
Figure 16:
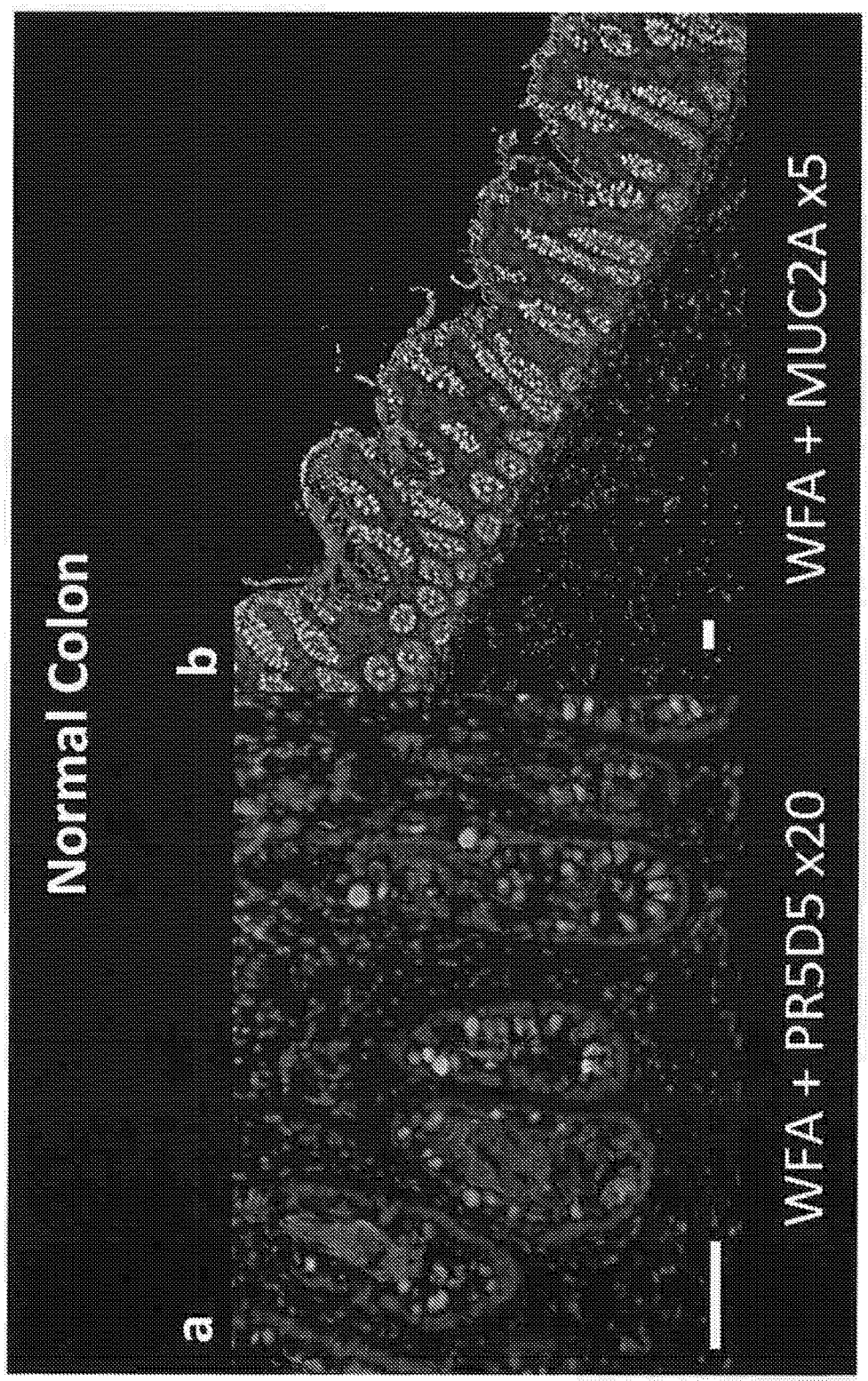
FIG. 16—shows further examples of immunofluorescence FFPE section of normal human colonic epithelium stained with DAPI (blue), WFA-fluorescein (green), and PR5D5 (left, red) ×20 objective or MUC2A (right, red) ×5 objective, showing that WFA binds to secreted mucus within the lumens of the crypts (left) and to goblet cells and mature mucus lining the top of the colonic epithelium (right). Scale bars 200 μm.

As MUC2 is the predominant component of mucus produced by goblet cells experiments were undertaken to demonstrate that MUC2 is the major protein binding to MUC2. Western blotting with WFA lectin and a MUC2 specific monoclonal antibody demonstrated that WFA recognized a glycoprotein that was the same molecular size as MUC2, and was present in normal samples, but was significantly reduced in the paired cancer specimens (FIG. 14). To confirm the interaction between WFA and MUC2 co-immunofluorescence staining using 2 different MUC2 antibodies (MUC2(A) and MUC2(D)), and the antibody PR5D5, which identifies mucin in goblet cells, was performed (FIG. 2, FIG. 15, FIG. 16 and FIG. 17a). MUC2(A) and WFA both stained goblet cell theca, although there was a lack of WFA staining at the bottom of the crypts, strongly suggesting that WFA binds to more mature or fully glycosylated forms of MUC2. MUC2(D) localised to the ER adjacent to the goblet cell theca, consistent with it identifying the MUC2 protein backbone. WFA and PR5D5 showed a significant degree of overlap, although there was more WFA binding to the mucin located in the lumens of the crypts (FIG. 16), suggesting that WFA may bind to the more mature or fully glycosylated, unpacked forms of mucin compared to PR5D5, which mainly stains mucin within goblet cell granulae.

Figure 17:
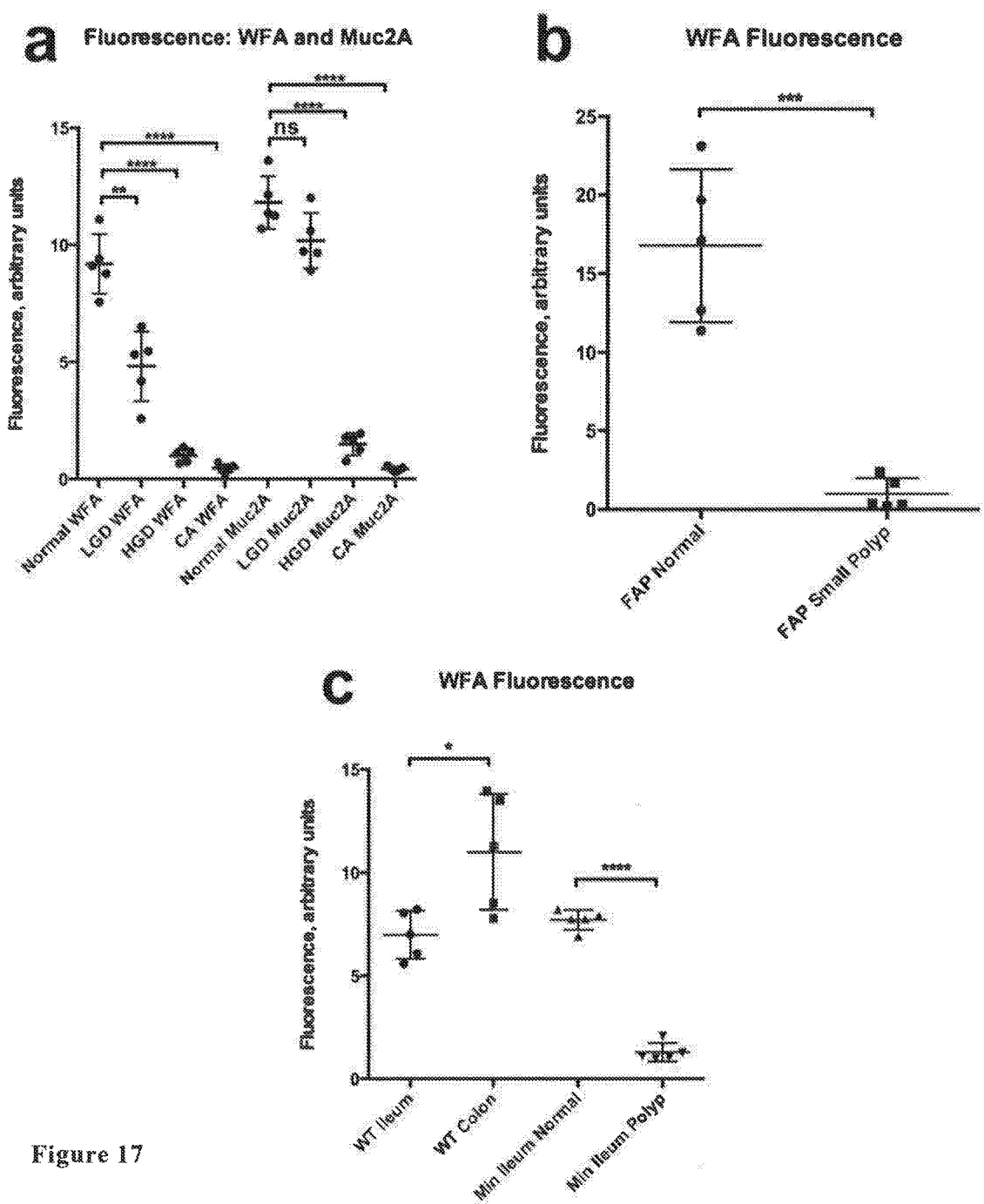
FIG. 17—shows the quantitation of fluorescence. Quantitation of WFA and Muc2A fluorescence of further FFPE images relating to FIGS. 3, 4 and 5. n=5 for each group, (**p<0.0001, *p<0.001, **p<0.01, *p<0.05, ns=not significant)
Figure 17:
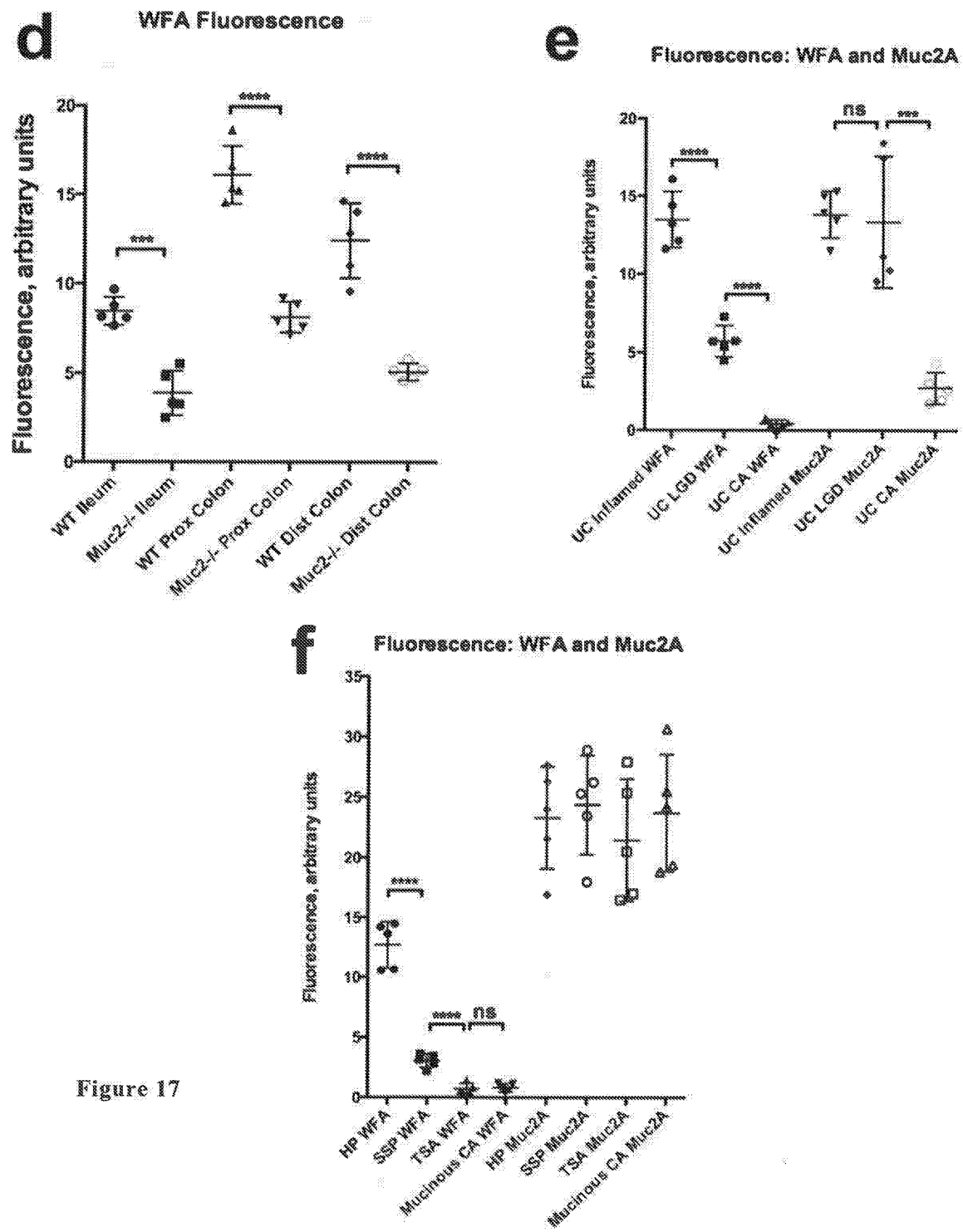

Dysplastic tissue and cancer tissue was then examined using these three antibodies, and it was noted that whilst WFA binding was reduced in low-grade dysplasia, MUC2 protein expression was still present at this stage (FIG. 2, FIG. 17a). However, both MUC2 expression and WFA binding were lost in HGD and cancer. This suggests that changes in MUC2 glycosylation, as detected by WFA binding, occur before changes in the expression levels of the MUC2 protein backbone.

To investigate whether the loss of WFA binding is an early phenomenon during carcinogenesis, the staining pattern of WFA and MUC2 on small polyps from Familial Adenomatous Polyposis (FAP) patients was examined (FIG. 3a, FIG. 17b). Whilst adjacent normal epithelium stained strongly for both WFA and MUC2A, small adenomas in FAP lost both MUC2A and WFA staining even at an early stage. Experiments were also undertaken to investigate whether the differential binding of WFA occurred in the Multiple Intestinal Neoplasia (Min) mouse model of FAP (FIG. 3b, FIG. 17c). Min mice are heterozygous for a truncating Apc mutation, and spontaneously develop multiple adenomas in the small and large intestine. As with human tissue, WFA was found to bind strongly to mucus and goblet cells in normal epithelium of Min mouse, but not to adjacent dysplastic polyps, suggesting that the glycosylation changes that occur during carcinogenesis are conserved between species.

To assess what degree of WFA staining is due to binding to MUC2, WFA fluorescence in Muc2 knock-out mice was examined. The data show a substantial reduction in binding of WFA in areas where goblet cells would be expected to be seen in Muc2 knock-outs. There is some residual binding to brush border epithelium, most likely to GalNAc residues on non-Muc2 glycosylated proteins (FIG. 3c, FIG. 17d and FIG. 18).

To confirm the specificity of WFA binding to goblet cells, immunofluorescence was performed on two colorectal cancer cell lines, SW1222 and HCT116. SW1222 has the capacity to differentiate to all three epithelial lineages, whereas HCT116 cell line consists of mainly cancer stem cells that lack the ability to differentiate and does not form goblet cells. Whilst WFA bound to SW1222, and co-localised with Muc2 and PR5D5 staining, WFA did not bind to HCT116, which did not express Muc2 nor bind to PR5D5 (FIG. 19), confirming that a lack of goblet cells is responsible for the lack of WFA binding.

Clinical Relevance of Fluorescently Labelled WFA on FFPE

As the endoscopic differences between dysplasia and inflammation can be subtle, experiments were undertaken to determine whether WFA could distinguish dysplasia on a background of ulcerative colitis (UC). In FFPE sections, while WFA bound to non-dysplastic inflamed tissue, its binding was reduced in dysplastic tissue, and both WFA binding and MUC2 protein expression were clearly reduced in cancerous lesions (FIG. 4 and FIG. 17e) making WFA a useful diagnostic tool for cancer screening even in UC.

The subtle differences in morphology between HPs and SSPs also present specific diagnostic challenges during conventional colonoscopy. Whereas HPs are benign lesions, SSPs are thought to be carcinoma precursors through the serrated pathway, highlighting the paramount importance of the development of a clinical tool that can distinguish between these two lesions. WFA was applied to a panel of FFPE sections, including HPs, SSPs, TSAs and mucinous cancers, and showed that whilst WFA bound to HPs, it did not bind to the other three types of lesions (FIG. 5, FIG. 17f, FIG. 20-23). However, MUC2 protein continued to be expressed at high levels by all 4 lesions based on MUC2A immunofluorescence, confirming that the loss of WFA binding is due to changes in glycosylation as opposed to loss of MUC2 expression or loss of functioning goblet cells. These findings teach that benign HPs may be distinguished from pathologically significant polyps by virtue of WFA binding, and demonstrate that changes in glycosylation, rather than MUC2 protein expression, are an early step in the development of SSPs and TSAs, as well as conventional adenomas.

Validation of WFA Using Fresh Tissue

Figure 6:
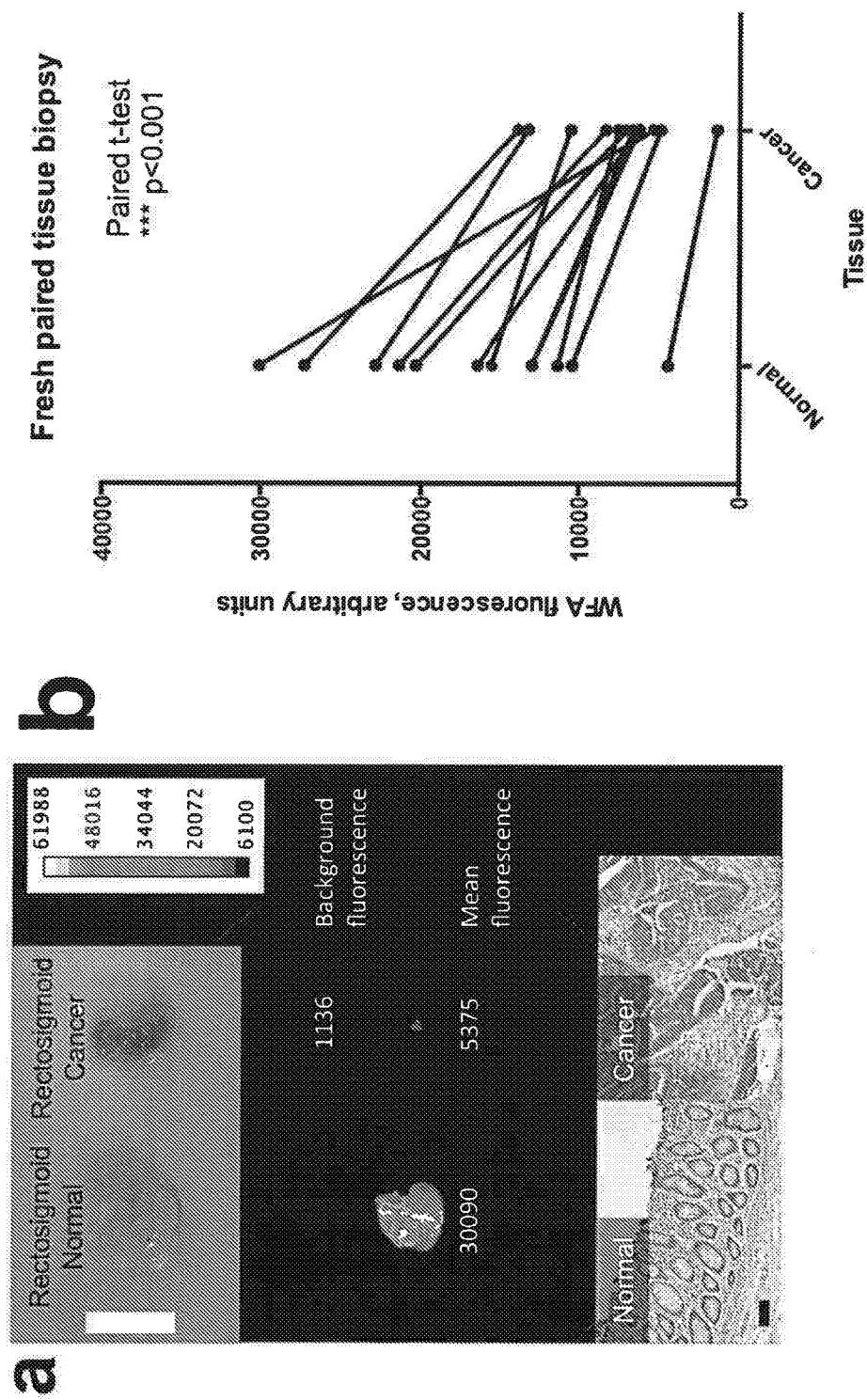
FIG. 6—shows the application of WFA to fresh incisional biopsy specimens.
Figure 7:
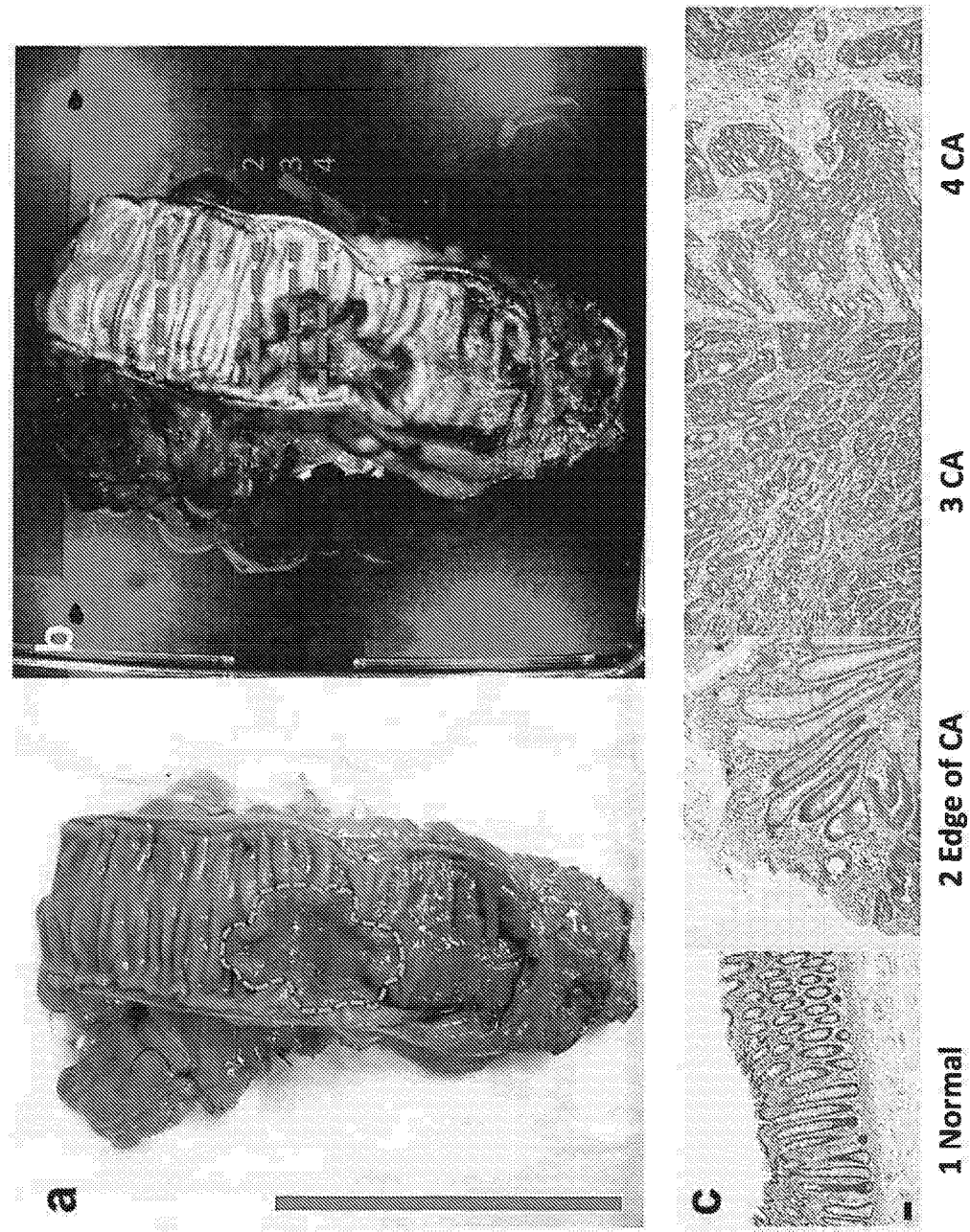
FIG. 7—provides validation of fluorescent WFA using whole organ fresh tissue: anterior resection of rectosigmoid cancer.

Fluorescein-labelled WFA was applied to fresh paired incisional biopsies of normal and cancer tissue from 12 patients (FIG. 6). The degree of fluorescence was captured using the IVIS 200 camera and then quantified, demonstrating that the fluorescence from normal tissue was higher than cancerous tissue (paired t-test, $p<0.001$). WFA was applied directly to freshly specimens within 30 minutes of resection, including an anterior resection (FIG. 7). WFA binding now showed clear demarcation between non-dysplastic and cancer tissue. However, a sigmoid colon specimen with diverticular disease (FIG. 24) clearly showed that diverticular disease did not alter the binding of WFA compared to adjacent normal mucosa. Quantitation of the fluorescence of these whole specimens and others is shown in FIG. 25. Using the IVIS 200 camera, the mean normal to cancer/dysplasia ratio was 2.6.

Figure 8:
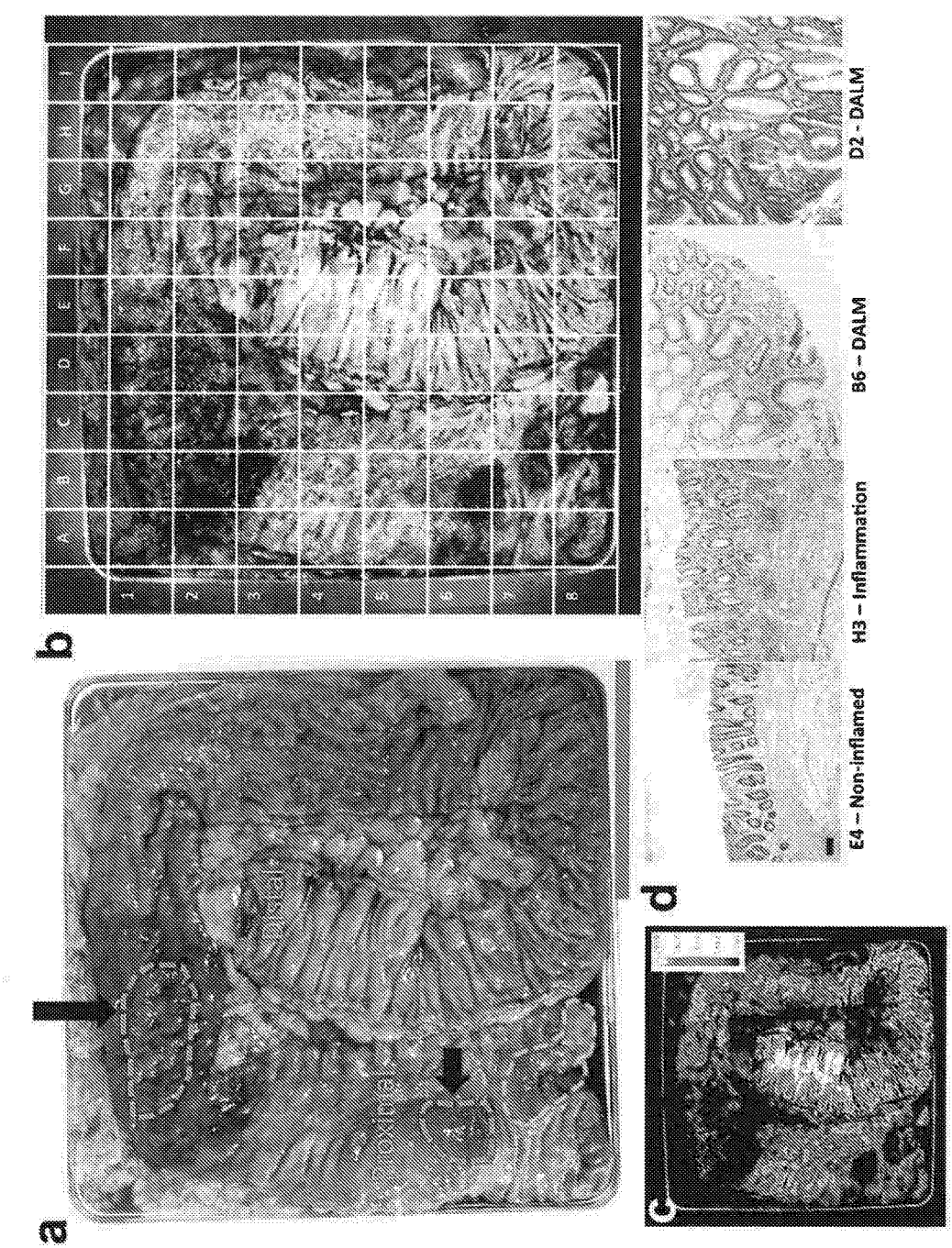
FIG. 8—shows whole fresh ex vivo imaging of a specimen obtained from a patient with ulcerative colitis and DALM.

Fluorescent WFA was applied to ex vivo freshly resected tissue from a patient undergoing resection for Dysplasia Associated Lesion or Mass (DALM), which is associated with an increased risk of developing carcinoma, and with distal sparing due to the use of steroid enemas (FIG. 8a). WFA was applied topically for 10 minutes onto the specimen, briefly rinsed twice and then imaged using the IVIS 200 camera (FIGS. 8b and c). WFA bound strongly to the non-dysplastic distal colon (FIG. 8b, Grid E4), and was able to detect both the large DALM (FIG. 8b, Grid D2) and another small flat DALM that was not noted on previous endoscopic examinations (FIG. 8b, Grid B6). These areas had lower levels of fluorescence compared to inflamed tissue with no dysplasia (FIG. 8b, Grid H3).

Figure 9:
FIG. 9—shows fresh ex vivo imaging of a transanal endoscopic microsurgery (TEMS) specimen.

The potential clinical use of WFA in identifying dysplasia in a transanal endoscopic microsurgery (TEMS) specimen from a patient with a previously resected cancerous rectal polyp requiring radiotherapy was investigated (FIG. 9). WFA was able to distinguish the areas of no dysplasia (FIG. 9b, Grids G1, G2 and D3), low-grade dysplasia (FIG. 9b, Grid C3) and fibrosis with underlying residual cancer (FIG. 9b, Grid C2). In this specimen, the area of cancer was very close to the resection margin. This demonstrates the potential utility of WFA in identifying abnormal tissue and therefore guiding resection margins during endoscopic surgery.

To confirm the observations of reduced WFA binding in TSAs in FFPE sections, whole specimen imaging of a freshly resected TSA was performed, which demonstrated minimal binding of WFA using the IVIS 200 camera (FIG. 26).

Figure 10:
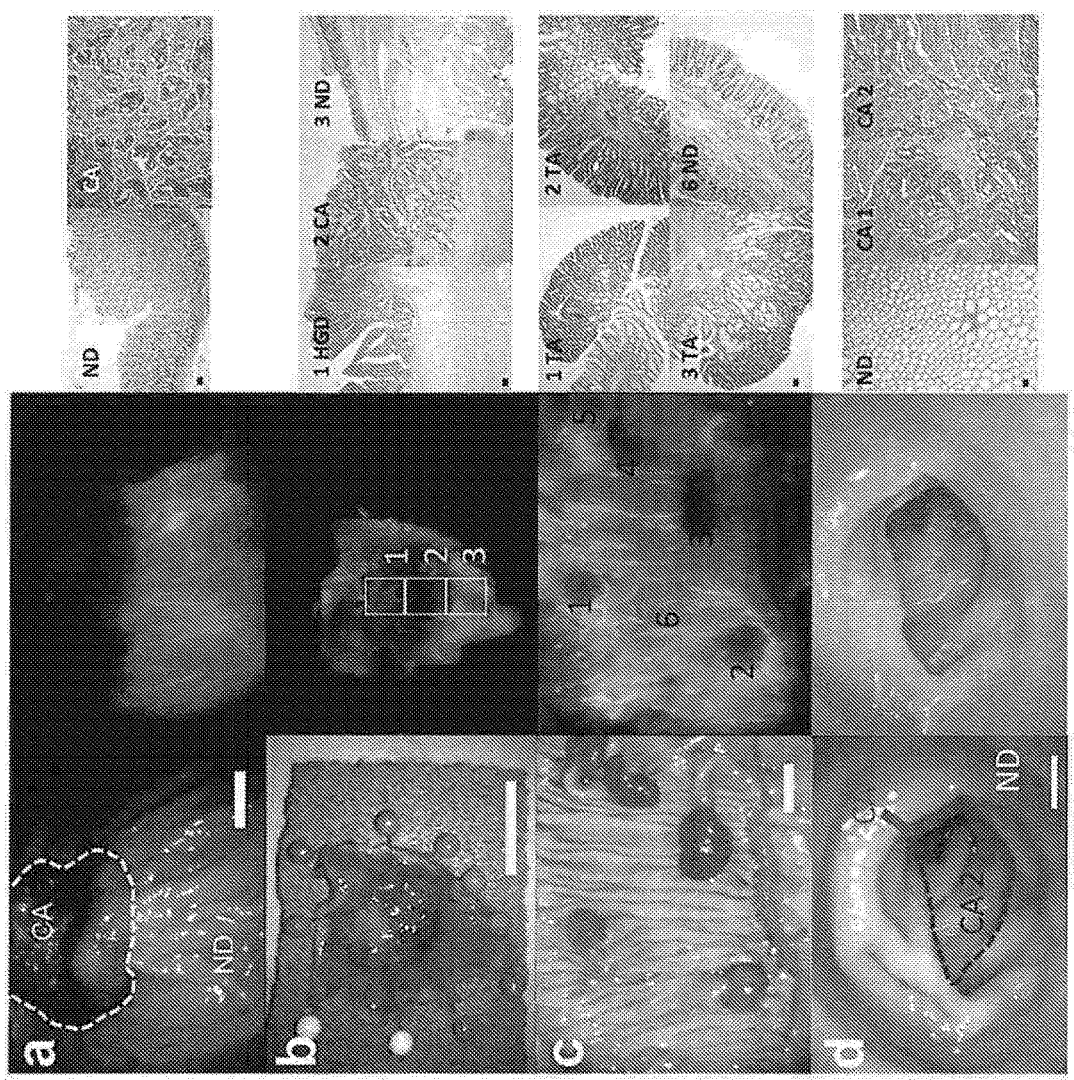
FIG. 10—illustrates white light and fluorescence imaging using a 660 nm fluorescence endoscope system after application of WFA-Cy5.

Imaging of Fresh Specimens Labelled with WFA Using a Fluorescent Capable Clinical Endoscope System As proof of principle, fresh specimens were imaged ex vivo using a fluorescent enabled endoscope with an excitation wavelength of 660 nm to minimise interference from tissue autofluorescence. WFA-Cy5 and WFA-fluorescein were shown to co-localize (FIG. 27). After obtaining baseline white-light endoscopic and auto-fluorescence images, Cy5-labelled WFA lectin was topically applied to the mucosal surface for 10 minutes, rinsed briefly twice and then visualised. Representative video stills are shown in FIG. 10. The first specimen was an anterior resection with a rectosigmoid cancer, and WFA was clearly able to distinguish the border between non-dysplastic and cancerous tissue (FIG. 10a). The second specimen was a TEMS resection, and WFA-Cy5 was able to distinguish normal mucosa from high grade dysplasia and invasive cancer as demonstrated by decreasing levels of fluorescence (FIG. 10b). The third specimen was an anterior resection from a patient with multiple left-sided colonic polyps but no previous family history of polyposis (FIG. 10c), with tubular adenomas that fluoresced less compared to adjacent normal mucosa. Due to the size of this sample, the imaging system was used in wide-field mode. Our fourth specimen was from a patient with ulcerative colitis, DALM and two synchronous cancers (FIG. 28). WFA-Cy5 was able to distinguish a flat area of dysplasia from non-dysplastic tissue, even though this was not obvious on white light endoscopy.

To simulate colonoscopic conditions an anterior resection specimen was insufflated and intubated, allowing the mucosa surface to be visualized with a fluorescence endoscope (FIG. 10d). After application with WFA-Cy5, a large flat cancerous lesion was identified that was not visible on white light, but was identified by its low binding to WFA-Cy5. Similarly, a right hemicolectomy specimen was visualized under colonoscopic conditions, and WFA-Cy5 was able to identify a flat abnormal area of necrosis with cancer that was not apparent on white light imaging alone (FIG. 29).

Using the fluorescence endoscope system, the mean normal to cancer/dysplasia fluorescence ratio was 3.6 (FIG. 30). Repeated rinsing of up to 20 times was also shown not to substantially wash away WFA-Cy5, confirming that it binds strongly to the mucosal surface (FIG. 31).

Discussion

The results presented here show that the lectin WFA, and by analogy any agent capable of distinguishing between mature MUC2 glycosylation and incomplete or aberrant MUC2 glycosylation, binds more strongly to normal tissue compared to dysplasia and cancer tissue. A key requirement for any adjunct tool for endoscopy is the ability to distinguish clearly normal from abnormal tissue. It is demonstrated here that fluorescent WFA has the potential to be a clinically useful adjunct endoscopic tool for four reasons. Firstly, fluorescent WFA can be used to identify flat lesions that would otherwise be missed by white light endoscopy, for example, DALMs in a patient with ulcerative colitis. On white light endoscopy, it is virtually impossible to distinguish between inflammation and dysplasia, as highlighted by FIG. 8. Flat lesions adjacent to obvious tumors can also be missed, as highlighted by FIG. 10d and FIG. 29. Secondly, it can robustly distinguish HP from more significant polyps, such as SSPs/TSA/mucinous CA. This is an extremely important clinical finding as, up until now, no known marker has been shown to distinguish HPs from significant polyps. Whereas HPs can be managed conservatively, there is increasingly evidence that SSPs can progress to colorectal cancer via the serrated pathway. Therefore, the early identification of SSPs is critical in preventing the development of colorectal cancer. Thirdly, WFA can distinguish between low grade dysplasia and high grade dysplasia/early invasive cancer. Having a tool to help distinguish between these two conditions is clinically extremely useful as the former could be managed via endoscopic polypectomy, whilst the latter would require formal surgical resection of the affected bowel and thus require a much more invasive procedure. WFA could therefore characterize polyps at the time of endoscopy and help decide the most appropriate management post procedure. Fourthly, WFA can help guide resection margins during endoscopic polypectomy or during transanal endoscopic microsurgery (TEMS), particularly in patients who have undergone previous procedures and in whom it would be extremely difficult to judge which areas need to be removed based on white light endoscopy alone, as highlighted by FIG. 9.

The results presented here demonstrate that it is a change in glycosylation of MUC2 occurring early in the development of dysplasia that is responsible for the reduced WFA binding, as MUC2 protein expression is still present in low grade dysplasia. This has not been described before.

The data presented here strongly suggests that the major binding target of WFA in the colon and rectum is mature glycosylated MUC2 in the upper portion of colonic crypts and in secreted mucin. However, WFA does not bind to the bottom of the crypts where the forms of MUC2 are immature.

The data demonstrates that fluorescently labelled WFA may be used to help guide resection margins during endoscopic mucosal resections and TEMS, particularly in identifying flat, subtle lesions or dysplasia. This may be possible even on a background of ulcerative colitis when such lesions may otherwise be missed on white-light endoscopy. Failure to detect residual polyp tissue after polypectomy, with a risk of development of interval cancer, may be more common than previously suspected, occurring in 31% of cases for serrated lesions and 17% of cases for large (10-20 mm) adenomas in a recent large US study. The data also shows that specific glycosylation changes occur in the development of significant lesions including SSPs, TSAs and mucinous cancers, though not in benign HPs. The exploitation of these glycosylation differences to distinguish HPs from significant polyps has not been described before and would potentially be very useful clinically, particularly given the difficulty in differentiating HPs from SSPs using conventional white-light endoscopy or advanced endoscopic imaging techniques such as narrow band imaging. The early detection of SSPs is especially important since it is a precursor lesion in the serrated pathway of colorectal cancer.

Using a 660 nm fluorescence endoscope, an average normal to cancer/dysplasia fluorescence ratio of 3.6 was observed.

The ex vivo specimens used for the preliminary assessment of fluorescence enabled endoscopy were freshly resected colorectal whole organs imaged within 30 minutes of retrieval, and performed in conditions intended to simulate in vivo endoscopic visualisation. The binding affinity (Kd) of WFA lectin to glycans is strong (between 0.01 to 1.0 nM). The data shows that WFA binds tightly to colorectal mucosa, as the fluorescence signal was still bright after repeated washings of up to 20 times were performed on labelled fresh tissue (FIG. 31). The results are clearly very promising for the development of in vivo fluorescence enabled endoscopy using lectins as molecular imaging tools. The topical application of lectins would be similar in technique to the application of chromoendoscopic dye, which is routinely performed.

The lowest oral toxicity dose of WFA in humans is 710 µg/kg, and in a 75 kg person, this would equate to 53.25 mg. In these experiments, WFA was topically applied on fresh tissue at a concentration of 5 µg/mL, typically using 20 mL of solution. This is less than 1/500th of the lowest oral toxicity dose, assuming that all of the compound would be absorbed in the colon, which would be unlikely as most absorption would be in the small gut. In practice, the WFA will be applied topically to colon and will bypass the small intestine.

Methods

Cell Lines and Cell Culture

The origins and culture conditions of all the cell lines used have been described previously 36. The cell line panel was chosen to reflect comparable numbers of replication error deficient (RER+) (n=14) cell lines and replication error proficient (RER−) (n=16) cell lines. RER+ cell lines: CCK81, DLD1, Gp2d, HCA7, HCT116, HCT15, LOVO, LS180, LS174T, LS411, RKO, SNUC2B, SW48, and VACOS. RER− cell lines: C80, C84, C99, CC20, COL0741, HRA19, HT29, LIM1863, LS513, NCIH716, PCJW, RCM1, SKCO1, SW1222, SW1417, and WIDR.

Gene Expression Microarrays

Total RNA was extracted by using the RNeasy mini kit (Qiagen) according to the manufacturer's instructions. Twenty micrograms of RNA of each sample were sent to the Molecular Biology Core Facility of the Paterson Institute for Cancer Research for gene expression microarray analysis using the Human genome U133+2 chips following the manufacturer's instructions (Affymetrix). Microarray data were analyzed using Partek Genomics Suite software. The data were log 2-transformed, RMA-normalized (with GC correction), using quantile normalization with Median Polish for Probeset summarization as optional settings in the software. Differentially expressed genes were identified by low probabilities from a t-test comparing mean-expression levels of the cancer cell lines (n=30) versus normal controls (n=20). P values were corrected for multiple testing, as implemented in the Partek software.

Immunohistochemistry of Formalin Fixed and Fresh Frozen Specimens

Formalin fixed and fresh frozen samples of normal colonic mucosa, dysplastic tissue and colorectal cancer were obtained from the Department of Clinical Pathology, Oxford University Hospitals, UK. The diagnoses of all specimens were confirmed by a consultant histopathologist (LMW). The materials used were approved by the Oxfordshire Clinical Research Ethics Committee. For FFPE blocks, specimens were sectioned into 4 µm thick slices and mounted onto microscope glass slides (Menzel-Glaser Superfrost Plus). Sections were deparaffinised in Histoclear twice for 3 minutes, and hydrated in 100% ethanol, 100% Industrial Methylated Spirit (IMS) and 70% IMS for 2 minutes each. Slides were then rinsed in distilled water. Antigen retrieval was performed using the Dako Target Retrieval solution at 100° C. for 20 minutes, followed by cooling to room temperature for 1 hour. Slides were then washed twice in PBS and once in 0.5% PBS-Tween for 5 minutes each. Tissue specimens were then encircled using the hydrophobic ImmEdge pen (Vector Labs) and blocked for 30 minutes using Invitrogen blocking reagent (0.1 g/10 mL PBS-Tween).

Slides were then incubated with the fluorescently labelled lectin in the dark at 37° C. for 10 minutes, followed by two washes with PBS-Tween. Fluorescently labelled (fluorescein or rhodamine) and biotinylated lectins *Wisteria floribunda* (WFA), *Dolichos biflorus* (DBA), *Amaranthus Caudatus* (ACL), *Bauhinia Purpurea* (BPL), *Vicia Villosa* (VVL) and *Sophora Japonica* Agglutinin (SJA) were purchased from Vector Laboratories, Burlingame, USA and were used at a dilution of 1:200 (10 m/mL). Competitive binding assays were performed by incubating WFA lectin with excess free GalNAc sugar (200 mM, Vector Labs) for 12 hours at 4° C.

Co-staining was performed using primary antibodies PR5D5 (in-house mouse mAb) 1:200, MUC2(A) Abcam (EPR6144) 1:250 rabbit mAb, MUC2(D) Dako (clone CCP58) 1:100 mouse mAb, incubated overnight at 4° C. Secondary antibodies included goat anti-mouse HRP (1:100 Invitrogen), goat anti-rabbit HRP (1:100 Invitrogen) and streptavidin HRP (1:100 Invitrogen) incubated at room temperature for 1 hour, followed by Tyramide Alexafluor 568 (Invitrogen) for 10 minutes. Coverslips were mounted onto the tissue specimens using Vectashield mounting medium containing DAPI (Vector Laboratories, Burlingame, Calif., USA). These slides were examined using a Zeiss Axioscope 2 Plus microscope, a Zeiss Axio Observer microscope and a Zeiss LSM 510 Meta confocal microscope. Representative images were captured with Axioscope and Zeiss ZEN software.

Immunohistochemistry of Cell Lines

SW1222 and HCT116 cell lines were plated at a density of $3 \times 10^5$ cells per well in Nunc single well chamber slides, grown for five days in media as described above, then fixed with ice-cold methanol followed by 2% formaldehyde for 5 minutes each. Slides were then washed twice in PBS and once in 0.5% PBS-Tween for 5 minutes each, then blocked for 30 minutes using Invitrogen blocking reagent. Slides were then stained with lectins and antibodies as described above for FFPE sections.

Human Tissue Lysate

Fresh mucosa from normal tissue and paired cancer specimens were finely minced in chilled lysis buffer (1% NP-40, 0.5% sodium deoxycholate, 1 mM EDTA, 150 mM NaCl, 50 mM Tris base, pH 8.3), followed by ultrasonication for 15 minutes on ice. The supernatant of this extract was used for experiments. Protein quantification was performed using a standard BCA kit (Pierce).

Gel Electrophoresis

Protein samples were run in a vertical electrophoresis unit (Invitrogen). 30 micrograms of protein were mixed with 4× Laemmli sample loading buffer, then denatured at 70° C. for 10 minutes. A 10-well 3-8% Tris-Acetate Gel (NuPAGE® Novex® Pre-Cast Gel, Invitrogen) was placed in the vertical electrophoresis unit, and immersed in 1× NuPAGE® Tris-Acetate SDS running buffer. Each of the wells was washed with running buffer before loading the protein samples and 10 µL of HiMark pre-stained molecular weight marker (Invitrogen). The loading samples were then resolved in the gel at 150 V for 60 minutes.

Western Blotting

PVDF membrane was used for immunoblotting. The membrane was pre-soaked in methanol. The 1× transfer buffer consisted of 50 ml of 20× transfer buffer (Invitrogen), 750 ml of MilliQ water and 200 ml of methanol. Proteins were transferred from the gel to the membrane by electrophoresis in transfer buffer at 360 milliamps for 90 minutes on ice (BioRad system, USA). After transfer, the membrane was rinsed in PBS-T, and blocked with 5% Marvel in PBS-T for 1 hour at room temperature on a rocking platform. The membrane was then incubated with the appropriate primary antibody in blocking solution for 1 hour at room temperature. After three 5-minute washes with PBST, the membrane was incubated with horse-radish peroxidase (HRP) conjugated secondary antibody in blocking solution for 1 hour at room temperature. The membrane was washed three times for 5 minutes each with PBS-T. The antibody signal was amplified using chemiluminescence (Amersham ECL Prime Western Blot Detection Reagent, GE Healthcare, UK), and incubated for 5 minutes in the dark with ECL solution A and B at a ratio of 1:1. Excess ECL solution was removed and the membrane was exposed to a sheet of Fujifilm (Tokyo, Japan), which was then developed using an SRX-201 film processor (Konica Minolta, Tokyo, Japan).

Primary antibodies and lectins used included WFA—Biotin 1:200 (Vector), MUC2 1:100 (mouse mAb DAKO) and Actin 1:1000 (rabbit pAb Sigma-Aldrich). Secondary antibodies used included streptavidin-HRP 1:2000 (Invitrogen), rabbit anti-mouse HRP 1:10,000 (Dako) and swine anti-rabbit HRP 1:2000 (DAKO).

Calculation of Fluorescent Levels and Statistical Analysis

The degree of binding of lectin was assessed by comparing the amount of fluorescence between paired samples of normal and cancerous tissue from each case, for both colorectal tissue microarray and fresh tissue specimens. Images were analysed using ImageJ (National Institutes of Health). For each image, the average background level of fluorescence was calculated from 3 readings and subtracted from the mean fluorescence level of the mucosal layer, also calculated from 3 readings. The adjusted fluorescence was then used for statistical analysis. Paired t-tests were performed using GraphPad Prism version 5 for Mac OS X, GraphPad Software, San Diego Calif. USA, www.graphpad.com.

Fresh Tissue Analysis

Fresh incisional biopsies and whole organ tissue were obtained from the Oxford Radcliffe Biobank in accordance with the local ethics committee. The lectins were topically applied to the specimens ex vivo and incubated at 37° C. for 10 minutes to simulate in vivo colonoscopic conditions. Samples were then rinsed twice with PBS, and images were captured using IVIS 200 fluorescent capable camera (Caliper Life Sciences). IVIS Camera settings: exposure time 1 sec, excitation wavelength (GFP filter) 445-490 nm, emission wavelength (GFP filter) 515-575 nm, binning factor 4.

Conjugation of Wisteria floribunda Lectin to Cy5

Wisteria floribuda lectin (L-1350, Vector laboratories Ltd., UK) was labelled with Cy5 dye (PA25001, monoreactive dye, GE Healthcare, UK) at 15 times molar excess of dye to protein in Bicine buffer (100 mM, pH 8.5) for 2 hours at room temperature. Labelled lectin was separated from free dye on PD-10 column (17-0851-01, GE Healthcare, UK) and analysed on a nanodrop spectrophotometer. Optical densities at 280 nm and 650 nm were used to approximate concentration and labelling ratio of lectin.

660 nm Fluorescence Endoscope

The Cy5-labelled WFA lectin solution was applied at a concentration of 5 µg/mL onto freshly excised tissue samples and rinsed twice with PBSA. All imaging was performed at an excitation wavelength of 660 nm, at a power density in the range 1-3 mWcm-2, delivered to the tissue surface through the ring illumination port of a Storz Hopkins II 10 mm diameter rigid laparoscope. White light illumination, derived from a white light emitting diode, was also provided through the same port. Detection was performed with an in-house developed detection system using a solid-state (CCD) video rate camera operated with integration times of 20-160 ms. Its output was digitised with the DFG/USB2pro image capture system (The Imaging Source, Germany). Video editing was performed using the Adobe Premiere Pro CS 5.5 (San Jose, Calif., USA) programme.

Mouse Tissue

The animals used in this study were ApcMin, Muc2−/− and wild-type mice that had been maintained on C57Bl/6 background for ≥6 generations. All procedures were carried out either in accordance to Home Office UK regulations and the Animals (Scientific Procedures) Act 1986 or approved by the Swedish Laboratory Animal Ethical Committee in Gothenburg. All mice were housed in standardized conditions of temperature (21-22° C.) and illumination (12 h light and 12 dark) with food and water provided ad libitum.

Mice were sacrificed by cervical dislocation. The intestinal tract was removed immediately and divided into small intestine and large intestine. The intestines were opened longitudinally, washed in PBS, fixed overnight in 10% neutral buffered formalin (NBF) and embedded in paraffin. For the Muc2−/− experiments, intestines were fixed in Carnoy's fixative (60% dry methanol, 30% chloroform, 10% glacial acetic acid) and then paraffin embedded.

The invention claimed is:

1. A method of determining the colorectal cancer status of a subject, comprising applying to the subject's colon and/or rectal surface an agent which binds to the mature glycosylated form of Mucin 2 (MUC2) such that it is able to distinguish between a) mature glycosylated forms of MUC2 and b) incomplete or aberrant glycosylated forms of MUC2, and determining the extent to which the agent binds, wherein the agent comprises a lectin or an antibody, and binding of the agent to the mature glycosylated form of MUC2 to colon and/or rectal tissue indicates normal, non-cancerous tissue and the absence of binding to the colon and/or rectal tissue indicates cancer tissue.

2. A method of treating colorectal cancer or dysplasia in a subject comprising:
   i) topically applying to the colon and/or rectal region of the subject a labeled agent capable of binding predominantly to either mature glycosylated forms of MUC2 associated with healthy tissue or to incomplete or aberrant glycosylated forms of MUC2 associated with dysplasia or cancer, wherein the agent comprises a lectin or an antibody;
   ii) visualizing the colorectal region to which the agent was applied and observing where the agent has bound; and
   iii) excising or treating tissue associated with the incomplete or aberrant glycosylated forms of MUC2.

3. The method of claim 2, wherein the agent is a lectin.

4. The method of claim 3, wherein the lectin is Wisteria floribunda agglutinin (WFA) or Dolichos biflorus agglutinin (DBA).

5. The method claim 1, wherein the agent is labeled.

6. A method of determining the colorectal cancer status of the colorectal region of a subject, comprising topically applying to the region a lectin and determining the extent to which it binds.

7. The method of claim 6, wherein the lectin is selected from WFA and DBA.

8. The method of claim 6, wherein the lectin binds predominantly to mature glycosylated MUC2 associated with normal tissue.

9. The method of claim 1, where colorectal cancer status includes one or more of: the presence or absence of colorectal cancer or colorectal dysplasia; the progression of colorectal cancer or colorectal dysplasia; the effectiveness or response of a subject to a treatment for colorectal cancer or colorectal dysplasia; and the prognosis for a subject with colorectal cancer or colorectal dysplasia.

10. The method of claim 1, wherein the agent is applied to a resected or biopsy sample of colorectal tissue ex vivo or to the colon or rectal surface of a subject in vivo.

11. The method of claim 1, wherein the agent binds predominantly to mature glycosylated MUC2 associated with normal tissue.

12. An agent which is able to distinguish between (a) mature glycosylated forms of MUC2 and (b) incomplete or aberrant glycosylated forms of MUC2, wherein the agent comprises a lectin or an antibody formulated for topical administration in a carrier comprising one or more of a thickener, lubricant and non-toxic nonionic surfactant.

13. A kit for identifying cancerous or dysplastic colorectal tissue, or for determining colorectal cancer status, in a subject comprising:
  i) a labeled agent comprising a lectin or an antibody which binds predominantly to either mature glycosylated forms of MUC2 or to incomplete or aberrant glycosylated forms of MUC2;
  ii) instructions to apply the labeled agent topically to the surface of the colon and/or rectal region of a subject, and
  iii) a carrier comprising one or more of a thickener, lubricant and/or a non-toxic nonionic surfactant.

* * * * *